United States Patent
Mongui et al.

(10) Patent No.: US 11,155,822 B2
(45) Date of Patent: Oct. 26, 2021

(54) TRANSPOSON THAT PROMOTES FUNCTIONAL DNA EXPRESSION IN EPISOMAL DNAS AND METHOD TO ENHANCE DNA TRANSCRIPTION DURING FUNCTIONAL ANALYSIS OF METAGENOMIC LIBRARIES

(71) Applicants: UNIVERSIDAD DE LOS ANDES, Bogotá (CO); CORPORACIÓN CORPOGEN, Bogotá (CO)

(72) Inventors: Alvaro Mongui, Bogotá (CO); Patricia Del Portillo Obando, Bogotá (CO); Silvia Restrepo Restrepo, Bogotá (CO); Armando Junca Howard, Cundinamarca (CO)

(73) Assignees: UNIVERSIDAD DE LOS ANDES, Bogota (CO); CORPORACION CORPOGEN, Bogota (CO)

( * ) Notice: Subject to any disclaimer, the term of this patent is extended or adjusted under 35 U.S.C. 154(b) by 337 days.

(21) Appl. No.: 15/573,952

(22) PCT Filed: May 14, 2015

(86) PCT No.: PCT/CO2015/000010
§ 371 (c)(1),
(2) Date: Aug. 2, 2018

(87) PCT Pub. No.: WO2016/180379
PCT Pub. Date: Nov. 17, 2016

(65) Prior Publication Data
US 2019/0017056 A1    Jan. 17, 2019

(51) Int. Cl.
C12N 15/65    (2006.01)
C12N 15/67    (2006.01)
(Continued)

(52) U.S. Cl.
CPC ............ *C12N 15/67* (2013.01); *C12N 15/10* (2013.01); *C12N 15/1082* (2013.01);
(Continued)

(58) Field of Classification Search
CPC ........ C12N 15/65; C12N 15/67; C12N 15/70; C12N 15/111
See application file for complete search history.

(56) References Cited

U.S. PATENT DOCUMENTS

| 6,159,736 A | 12/2000 | Reznikoff et al. |
| 2014/0162897 A1 | 6/2014 | Grunenwald et al. |

FOREIGN PATENT DOCUMENTS

| WO | 00/78977 A1 | 12/2000 |
| WO | 2010/049807 A2 | 5/2010 |
| WO | 2012/069668 A1 | 5/2012 |

OTHER PUBLICATIONS

Leggewie et al, J. Biotechnol. 123: 281-287, 2006.*
(Continued)

*Primary Examiner* — Kevin K Hill
(74) *Attorney, Agent, or Firm* — Lucas & Mercanti, LLP

(57) ABSTRACT

A transposon (TnC_T7) was developed to partially supply the transcriptional machinery during functional analysis of genomic/metagenomic libraries. This transposon was conceived and constructed to have the ability to integrate randomly into any episomal DNA, allowing the inducible expression of the adjacent DNA regions in both directions. In general, this genetic tool included a kanamycin resistance gene, two bidirectional T7 promoters and the T7RNA polymerase-coding gene, the latter under the regulation of the inducible arabinose promoter ($P_{BAD}$). The experimental validation confirmed the TnC_T7 potential to be used in functional genomic/metagenomic studies, in order to partially overcome the limitations of the bacterial hosts, which pre-
(Continued)

vent them to recognize most of foreign genes from DNA libraries.

5 Claims, 14 Drawing Sheets

Specification includes a Sequence Listing.

(51) Int. Cl.
    *C12N 15/70* (2006.01)
    *C12N 15/10* (2006.01)
    *C12N 15/11* (2006.01)
    *C40B 40/06* (2006.01)

(52) U.S. Cl.
    CPC ............ *C12N 15/111* (2013.01); *C12N 15/65* (2013.01); *C12N 15/70* (2013.01); *C40B 40/06* (2013.01)

(56) References Cited

OTHER PUBLICATIONS

Toreschel et al, Metagenomics 668: 117-139, 2010, Humana Press, Totowa, NJ, USA.*
Wang et al, J. Biotechnol. 189: 72-75, 2014; available online Sep. 2, 2014.*
Chao et al, Biotechnol. Prog. 18: 394-400, 2002.*
PBluescript II Phagemid Vectors Instruction Manual, Agilent Technologies, Inc, 2008.*
Finn et al, Gene Therapy 11: 276-283, 2004.*
Yan et al, J. Biotechnol. 44: 197-201, 1996.*
Serina et al, Res. Microbiol. 155: 692-701, 2004.*
Damron et al, Applied Environmental Microbiol. 79(2): 718-721, 2013; available online Nov. 2, 2012.*
J. McKinney et al., "Tightly Regulated Gene Expression System in *Salmonella enterica* Serovar Typhimurium," Journal of Bacteriology, vol. 184, No. 21, 2002, pp. 6056-6059.
L. Terron-Gonzalez et al., "Heterologous viral expression systems in fosmid vectors increase the functional analysis potential of metagenomic libraries," Scientific Reports, vol. 3, 2013, pp. 1107.
E. P. Culligan et al., "Metagenomics and novel gene discovery: Promise and potential for novel therapeutics," Virulence, vol. 5, No. 3, 2014, pp. 399-412.
E. Gabor et al., "Quantifying the accessibility of the metagenome by random expression cloning techniques," Environmental Microbiology, vol. 9, No. 9, 2004, pp. 879-886.
R. Warren et al., "Transcription of foreign DNA in *Escherichia coli*," Genome Research, vol. 18, 2008, pp. 1798-1805.
T. Aakvik et al., "A plasmid RK2-based broad-host-range cloning vector useful for transfer of metagenomic libraries to a variety of bacterial species," FEMS Microbiol Lett, vol. 296, 2009, pp. 149-158.
Z. Ivics et al., "Transposon-mediated Genome Manipulations in Vertebrates," Nat Methods., vol. 6, No. 6, Jun. 2009, pp. 415-422.
K. Datsenko et al., "One-step inactivation of chromosomal genes in *Escherichia coli* K-12 using PCR products," PNAS, vol. 97, No. 12, Jun. 6, 2000, pp. 6640-6645.
K. Riedel et al., "N-Acylhomoserine-lactone-mediated communication between Pseudomonas aeruginosa and Burkholderia cepacia in mixed biofilms," Microbiology, vol. 147, 2001, pp. 3249-3262.

* cited by examiner

Protein Expression = Phenotype

TRANSPOSON THAT PROMOTES FUNCTIONAL DNA EXPRESSION IN EPISOMAL DNAS AND METHOD TO ENHANCE DNA TRANSCRIPTION DURING FUNCTIONAL ANALYSIS OF METAGENOMIC LIBRARIES

CROSS-REFERENCE TO RELATED APPLICATIONS

This application is a National Stage of International patent application PCT/CO2015/000010, filed on May 14, 2015, which is incorporated herein by reference in its entirety for all purposes

FIELD OF THE INVENTION

The present invention relates to the development of transposons to partially supply the transcriptional machinery during functional analysis of genomic/metagenomic libraries, and therefore, to enhance the identification of novel compounds with biotechnological potential from genomic/metagenomic DNA libraries, partially overcoming the limitations of the bacterial hosts, which prevent them to recognize most of the foreign genes from DNA libraries.

BACKGROUND OF THE INVENTION

Currently it is estimated that one percentage of all microorganisms present in a natural environments can be cultured in standard laboratory conditions, and therefore, the great potential for novel compounds, enzymatic activities and genetic regulators useful to industry from the greater proportion of organisms in the biosphere is still unknown.

In view to the above, i.e., due to the limitations to characterize a higher proportion of enzymes and metabolites produced by non-culturable bacteria, metagenomics has emerged as an alternative approach to conventional microbiological analysis. This strategy is based on extraction of total DNA from an environmental sample (microbial community genome mix known as metagenome) and its subsequent cloning into easily culturable bacteria. With this approach genomic/metagenomic libraries have been constructed and used to identify bacterial isolates with their genetic information to produce novel enzymes and metabolites. Functional analyses are then performed based on the heterologous expression of foreign DNA, which is reflected in a particular trait (phenotype) expressed by some bacterial isolates of the genomic/metagenomic library.

Therefore, functional analyses of most of DNA libraries rely on efficient expression of heterologous genes in the bacterial host, for the identification of functions derived from known-unknown genes or from complex genetic clusters. The success of a given functional assay will largely depend on the detection method and the activity of interest. Three general types of screening can be distinguished: 1) Direct activity detection, where expression of a particular enzyme or metabolite is used to identify bacterial clones; 2) Modulated detection, which involves expression of genes required for bacterial growth under selective conditions; and 3) Substrate induction, as a strategy that promotes gene expression in the presence of a given substrate.

However, independent of the type of screening, functional analysis are often troublesome due to the fact that identification of desired phenotypes depends on many factors, such as the host-vector system selected, the size of the gene (individual or a gene cluster) of interest, its abundance in the metagenomic source, the detection method used and the efficiency of heterologous gene expression in the selected host.

In most genomic/metagenomic studies *E. coli* has been the preferred host for library construction and functional screening. This is largely due to the current understanding of the molecular genetics of this bacterium and its wide use as model for decades in areas such as microbiology and molecular biology. Moreover, the development and implementation of sophisticated genetic modification techniques, together with its simple manipulation, rapid growth, ease of processing and versatility in a wide range of genetic tools had made *E. coli* the preferred host in molecular biology experiments.

Beside these advantages, the genetic machinery of *E. coli* may be incapable of correctly perform gene expression of foreign DNAs. Metagenomes are complex mixtures of genomes from wide ranges of microorganisms and even a single genomic library could be obtained from a distantly related microorganism. Gabor et al. quantified the theoretical probability of *E. coli* to express genes from randomly cloned fragments of 32 prokaryotic complete genomes (Env. Microbiol. 2004, 6:879-886). This was determined in silico based on the presence of *E. coli* functional signals in these genomes and the length of the genomic inserts. Using three theoretical gene expression models, it was found that in average 40% of enzymatic activities encoded by prokaryotic genomes could be accessible to the *E. coli* machinery. This means that a significant proportion of genes from these genomes (60%) would be still incompatible for the transcriptional and translational machineries of the bacterial expression system.

A more recent analysis for assessing the ability of *E. coli* to globally transcribe different genes, both prokaryotic and eukaryotic, was evaluated by microarray and RT-PCR (Warren R L, et al.; Genome Res. 2008, 18:1798-1805). It was observed that *E. coli* was able to transcribe around half of *Haemophilus influenzae* genes, a smaller proportion of genes from *P. aeruginosa* and only a minimal number of human genes. Additionally, the genes that showed significantly higher transcription levels in *E. coli* had promoter regions related to sigma-70 subunit recognition sites from the bacterial RNA polymerase, highlighting the selectivity of the host transcriptional machinery during the first steps of foreign DNA expression.

Therefore, the selectivity of the transcriptional machinery is evident during the initial stages of foreign DNA expression, implying that any strategy aimed at increasing gene expression in functional genomic/metagenomic studies, independent of the chosen bacterial host, have to overcome this initial limitation.

Different strategies have been reported to improve the heterologous gene expression of genomic/metagenomic DNA. The use of alternative hosts, either the DNA library is built simultaneously in some of them or transferred from one host to another, has shown to be successful in increasing gene expression. This strategy is usually associated with the development of novel expression vectors that can be stably maintained in more than one bacterial system.

An example of development (but not functional implementation) of broad host or shuttle vectors was pSR44 (which was disclosed by Aakvik T. et al; FEMS Microbiol Lett 2009, 296:149-58). This vector can be induced from low to high-copy number with L-arabinose and contains a RK2 origin of transfer to allow conjugation in additional hosts like *Pseudomonas fluorescens* and *Xanthomonas campestris*. Although in recent years shuttle vector repertoire has increased, still few studies have confirmed the versatility of these genetic tools to enhance heterologous gene expression in functional analysis of metagenomic libraries.

Other modification on vectors used for construction of genomic/metagenomic libraries is the addition of promoters adjacent to the multiple cloning sites to enhance foreign DNA transcription. For obvious reasons, the effectiveness of this strategy is more restricted to libraries constructed with small DNA inserts. This is the case of pJOE930 plasmid, which having two inducible convergent lac-promoters on both sides of a symmetrical multiple cloning site allowed the identification of a large number of active bacterial isolates including lipolytic enzymes, amylases, phosphatases and dioxygenases (Lämmle K, et al.; J. Biotechnol. 2007, 127: 575-92).

Patent application WO 2012/069668 relates to the development of vectors and strains as expression systems offering the possibility of identifying genes of interest that are not expressed thereby in the bacteria hosting the metagenomic library, thus allowing detection of the functions encoded thereby, which, otherwise, would remain silenced and undetected. Specifically, said patent application discloses the inclusion of phage T7 derived promoter in cosmid and fosmid vectors to promote transcription of genomic/metagenomic inserts, as a result of the T7RNA polymerase (T7RNAP) expression from the host. The success of this strategy relies in the high processivity and efficiency of T7RNAP to transcribe genes, but it is restricted to the analysis of the flanking regions of genomic/metagenomic inserts.

Another promising approach is the use of mobile DNA elements or transposons, which have been widely used in a variety of advanced genetic studies such as mutagenesis, sequencing (US2014/0162897), genomic manipulation, transgenesis, gene therapy and functional modulation of gene expression (Ivics Z. et al.; Nat. Methods 2009, 6:415-22).

One of the best-characterized transposition machineries is the bacteriophage Mu. In contrast to the relative complexity of the in vivo transposition mechanism for this phage, which involves a number of auxiliary factors, it has been observed a substantially less conditions for the transposition reactions in vitro. Thus, the minimum reaction components for Mu transposition include the reaction buffer, the purified MuA transposase, the mini-Mu transposon and the DNA of interest (target DNA). These parameters have shown to be enough for efficient transposition events with low insertion bias on multiple target DNAs. All these features have made the implementation of Mu transposon an ideal and adjustable tool for different research fields.

In terms of applications in molecular biology Mu transposon has facilitated sequencing analysis, detection of polymorphisms and accurate determination of protein interactions. In the field of protein engineering Mu transposon has been basically used to generate truncated proteins to characterize differential enzymatic activities. At genomic level Mu transposons have widely promoted mutagenesis and transgenesis, looking to decrease or increase functional gene expression, respectively, in different organisms.

Specifically, Leggewie C. et al. (J. Biotechnol. 2006, 123:281-7) discloses the construction of the transposon MuExpress which randomly integrates in vitro into existing bacterial artificial chromosome (BAC) or cosmid libraries, allowing the inducible expression of its flanking regions in both directions, and permitting the bidirectional sequencing of the respective clones starting from unique primer binding sites.

Said MuExpress transposon was developed as a genetic tool to tackle the difficulty of gene transcription within long DNA inserts of metagenomic libraries. Theoretically this transposon increases the transcription level of fosmid DNA inserts because it includes at each of its ends a T7 promoter region reading outwards. However, a detailed analysis of the original MuExpress transposon design and construction revealed an important mistake that makes unviable the recognition of one of the two T7 promoter regions by the T7RNAP.

Another commercial transposon already known to randomly insert a single T7 promoter, but derived from Tn5 transposition system, is the EZ-Tn5<T7/KAN-2> (Epicentre-Illumina). However, neither MuExpress nor EZ-Tn5<T7/KAN-2>, which are based on T7RNAP high processivity transcription, reported enough evidence of transposon insertion and their relation with gene expression improvement. Additionally, MuExpress and EZ-Tn5<T7/KAN-2> transposons depend on bacterial hosts that express the T7RNAP (e.g. *E. coli* BL21 DE3, Invitrogen), which widely restrict its use in functional assays especially with metagenomic DNA, since most of the construction library kits rely on other specialized bacterial strains (e.g. *E. coli* Epi300, Epicentre-Illumina, Madison, Wis., USA).

Based on the versatility of Mu transposons in molecular biology-biotechnology research and the current need to efficiently improve the heterologous gene expression of genomic/metagenomic DNA libraries, novel genetic tools and strategies should be devised using this mobile DNA element.

SUMMARY OF THE INVENTION

The present invention involves the design of a novel Mu transposon and the methods to achieve an efficient expression of genes harbored in episomal DNAs from genomic/metagenomic libraries, that under traditional screening approaches are never detected in functional assays. The efficiency in the use of the invention is reflected in an increased proportion of bacterial isolates showing the desired phenotype, compared with the proportion of bacterial isolates that can be identified in original functional screenings. The first aspect of the invention is based on the sequential development of plasmids for the construction of the novel Mu transposon.

In one embodiment, the invention is directed to the development of a synthetic gene (Tn_A), which is an artificial DNA sequence as a result of specific combination of certain DNA elements, comprising:
  (i) one T7 promoter sequence
  (ii) one MuA transposase inverted repeat recognition site,
  (iii) multiple flanking recognition sites for restriction endonucleases.

In another embodiment, the invention is directed to the development of pUC57_Tn plasmid, which is an artificial vector as a result of specific combination of certain DNA elements, comprising:
  (i) a vector backbone with a high-copy number replication origin and a selectable marker,
  (ii) one T7 promoter sequence in an specific orientation,
  (iii) one MuA transposase inverted repeat recognition site in an specific orientation.

In another embodiment, the invention is directed to the development of pUC57_Tn_kanAB plasmid, which is an artificial vector as a result of specific combination of certain DNA elements, comprising:
  (i) a vector backbone with a high-copy number replication origin and a selectable marker,
  (ii) one T7 outward-reading promoter,
  (iii) one MuA transposase inverted repeat recognition site,
  (iv) a selectable marker different than the one located in the vector backbone.

In another embodiment, the invention is directed to the development of pBAD18-Cm_t7rnap plasmid, which is an artificial vector as a result of specific combination of certain DNA elements, comprising:
  (i) a vector backbone with a high-copy number replication origin and a selectable marker,
  (ii) a gene encoding the T7RNA polymerase regulated by an inducible promoter.

In another embodiment, the invention is directed to the development of pUC57_Tn_kanAB_t7 plasmid, which is an artificial vector as a result of specific combination of certain DNA elements, comprising:
  (i) a vector backbone with a high-copy number replication origin and a selectable marker,
  (ii) one T7 outward-reading promoter,
  (iii) one MuA transposase inverted repeat recognition site,
  (iv) a selectable marker different than the one located in the vector backbone,
  (v) a gene encoding the T7RNA polymerase regulated by an inducible promoter.

In another embodiment, the invention is directed to the development of pUC57_TnC_T7 plasmid, which is an artificial vector as a result of specific combination of certain DNA elements, comprising:
  (i) a vector backbone with a high-copy number replication origin and a selectable marker,
  (ii) a selectable marker different than the one located in the vector backbone,
  (iii) a gene encoding the T7RNA polymerase under an inducible promoter,
  (iv) two flanking T7 outward-reading promoters,
  (v) two flanking MuA transposase inverted repeats recognition sites.

In another embodiment, the present invention involves the development of F076_GFP fosmid, which is an artificial vector as a result of specific combination of certain DNA elements, comprising:
  (i) a fosmid backbone with low- to high-copy number replication origins and a selectable marker,
  (ii) a metagenomic DNA insert,
  (iii) a gene encoding the green fluorescent protein (GFP) variant with an upstream ribosome binding site (RBS), both specifically located inside the metagenomic DNA insert.

In another embodiment, the present invention is broadly directed to a method to enhance DNA transcription as the initial step of foreign gene expression, comprising:
  (i) generating an episomal transposition DNA library, as a result of the random insertion of the purified TnC_T7 transposon, wherein said episomal DNA includes plasmids, fosmids, cosmids or BACs,
  (ii) introducing the said episomal transposition DNA library of (i) into host cells,
  (iii) expressing the T7RNA polymerase encoded from the TnC_T7 transposon, to provide a bacterial host cell population with a diverse collection of episomal-derived DNA transcripts,
  (iv) screening said bacterial host cell population to identify bacterial isolates expressing a reporter gene or any other desired function.

In one embodiment, the present invention includes eight plasmids, which correspond to artificial vectors resulting from random TnC_T7 transposon insertions on pKR-C12 plasmid, each one comprising:
  (i) a vector backbone with its own selectable marker and a silent reporter gene,
  (ii) one differential TnC_T7 transposon insertion along the DNA sequence of (i).

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

Figure 14:
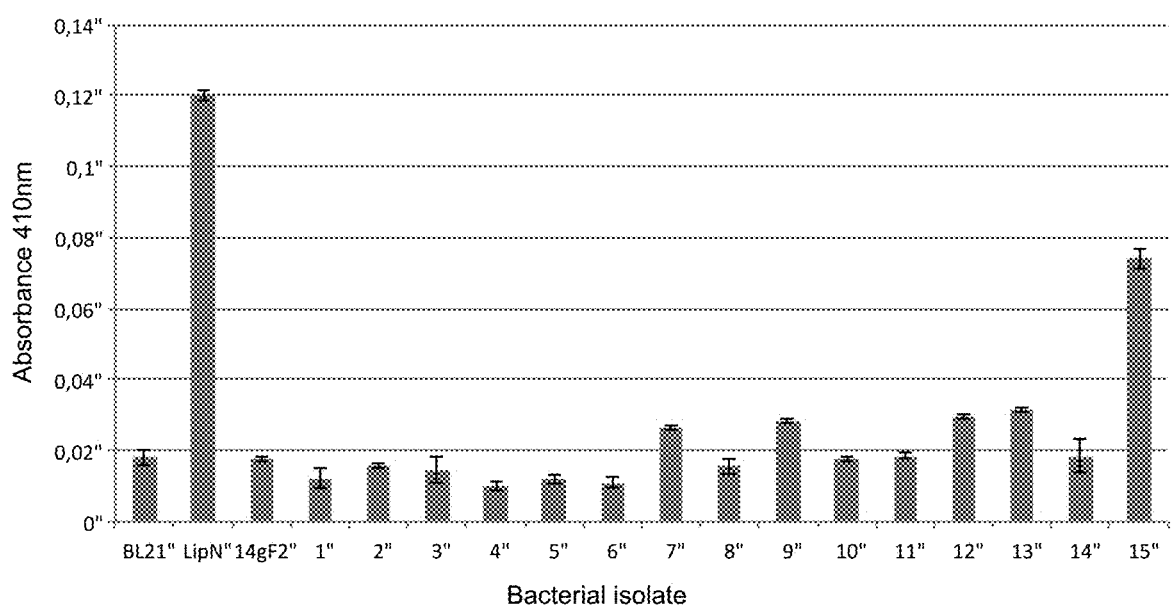

FIG. 14 outlines the degradation of 4-nitrophenyl butyrate from bacterial clone extracts. BL21, E. coli BL21 DE3 bacterial clone used as a negative control; LipN, E. coli BL21 bacterial clone transformed with pET100_LipN plasmid (bacterial clone kindly provided by Luis Peña—Molecular Biotechnology, CorpoGen, Bogota, Colombia) used as a positive control; 14gF2, E. coli Epi300 transformed with pCC2FOS_14 gF2 fosmid; 1-15, E. coli Epi300 bacterial isolates transformed with pCC2FOS_14 gF2 fosmid post transposition with TnC_T7.

DETAILED DESCRIPTION OF THE INVENTION

Definitions

Unless specifically defined or described in a different way elsewhere herein, the following terms and descriptions related to the invention shall be understood as given below.

As used herein, "artificial DNA" means a DNA sequence different from any found in nature or produced by non-natural processes, as the result of in vitro techniques or solid-phase DNA synthesis.

As used herein, "synthetic gene" means a DNA fragment synthesized in the laboratory by combining nucleotides without preexisting DNA sequences. In particular, the term refers to a completely synthetic double-stranded DNA molecule.

As used herein, "recognition sites" refers to locations on a DNA molecule containing specific sequences of nucleotides, which are recognized by specific proteins or enzymes.

As used herein, "restriction endonucleases" means enzymes that cut the double-stranded DNA molecules at specific recognition sites. The term referred in the present invention relates to restriction endonucleases or enzymes that specifically recognize DNA sequences of 6-8 nucleotides, in which the nucleotide sequence of one DNA strand reads in reverse order to that of the complementary DNA strand (palindromic).

As used herein, "transposable element" or "transposon" refers to a DNA sequence or a gene segment able to move from one genome or genetic position to be inserted in another (e.g. genome, chromosomes, episomal DNAs). The mentioned definition includes only transposable elements or transposons that are based on intermediate DNA molecules and that require the enzymatic activity of particular proteins denoted as transposases to be moved across different genetic positions.

As used herein, "transposition" or "transposition reaction" refers to a reaction wherein the transposon is inserted into a target DNA at random sites, through the catalytic activity of a transposase.

As used herein, "inverted repeat" means a sequence identified at the 5' or 3' termini or ends of transposons that are recognized specifically by transposases.

As used herein, "transposase" is intended to mean an enzyme that has the capacity to recognize and bind to a transposon end or transposon end sequences in a transposition reaction, to promote the mobilization of the transposon.

As used herein, "transposon insertions" means the specific locations where the transposon is inserted into a target DNA, as a result of the transposition reaction performed by a specific transposase.

As used herein, "target DNA" or "target vector" means a double stranded DNA that is suitable to be modified using molecular biology techniques. In this invention, the definition is associated to episomal DNA sequences that include specific recognition sites for restriction endonucleases or that can be modified by transposases as a result of the inclusion of transposable DNA elements.

As used herein, "DNA transcription" means the process of synthesizing a RNA copy from a DNA molecule. This corresponds to the first step of gene expression and is performed by a specialized enzyme, an RNA polymerase.

As used herein, "promoter" refers to a region on a DNA sequence in which a specific RNA polymerase can bind (e.g. the T7 promoter is recognized only by the T7RNAP), in order to start with the process of DNA transcription.

As used herein, "inducible promoter" means that the recognition of the promoter by the RNA polymerase, and therefore the transcriptional activity can be controlled in the absence or presence of chemical or physical factors. For purposes of the present patent, if a promoter is induced by a specific factor that will lead to specific protein synthesis (e.g. T7RNAP).

As used herein, "constitutive gene" or "constitutively expressed gene" means a gene that is transcribed continually at a relatively constant level. This term implies that a constitutive promoter regulates DNA transcription for the gene (e.g. kanamycin resistance gene), and therefore the constant expression of the resulting protein.

As used herein, "outward-reading" refers to the direction of DNA transcription from a specific promoter, which is located particularly inside a defined DNA sequence, as it can be a transposon, and that is located in the 5' or 3' ends of the DNA segment. In this case, reading outwards is restricted to DNA transcription processes from the mentioned promoter in which RNA synthesis starts but extends primarily towards the adjacent DNA from the transposon.

As used herein, "vector" refers to a double-stranded and circular DNA molecule used as a vehicle to artificially carry foreign DNA into a target bacterial cell.

As used herein, "artificial vector", refers to any artificial DNA as a vector, capable of self-replication inside a bacterial cell and therefore be stably maintained inside the bacterial host cell.

As used herein, "self-replication" and "episomal", in the present invention refer to the capability of a vector or an artificial vector not to be integrated in the genomic DNA of a certain cellular host, but to be automatically replicated in a host cell, and therefore be present when the host cell grows and divides. In particular, this term assumes the permanence of the vector or the artificial vector for several growth generations inside the host cell. This term includes plasmids, fosmids, cosmids and bacterial artificial chromosomes (BACs).

As used herein, "origin of replication" or "replication origin" refers to particular sequences in episomal DNAs at which replication is initiated, based on recruiting proteins involved in DNA replication.

As used herein, "transformation" means the process of introducing new genetic material specifically to bacterial cells. In the present invention the mentioned term is associated to introducing vectors, artificial vectors or modified artificial vectors to bacterial cells.

As used herein, "selectable marker" refers to a gene located inside bacteria (at genomic or episomal level) that confers a feature for artificial selection. The term is associated to antibiotic resistance genes (e.g. chloramphenicol resistance gene) located in vectors or artificial vectors for selection of bacterial isolates after transformation.

As used herein, "upstream" and "downstream" are terms used to differentiate relative positions in DNA or RNA sequences. Upstream is a position towards the 5' from another nucleic acid segment (e.g. promoter, gene, restriction site, etc.) in a single strand of DNA or in a RNA molecule. Downstream is a position towards the 3' from another nucleic acid segment in a single strand of DNA or in a RNA molecule.

As used herein, "metagenomic DNA" refers to the whole microbial-associated genomic DNA, isolated from complex samples like open natural environments (e.g. soil, water) or from microbiomes of multicellular organisms (e.g. humans).

As used herein, "insert" or "DNA insert" means a piece or fragment or sequence of DNA that is inserted, by molecular biology techniques, into a vector or an artificial vector for its subsequent selection, manipulation or expression in a host organism.

As used herein, "ribosome binding site" refers to an RNA sequence in which ribosomes can bind to initiate protein synthesis (translation) inside the host cell or organism, as part of the process of protein expression.

As used herein, "foreign gene expression" means the whole process by which the information of a particular gene is used to synthesize a functional gene product that for purposes of the present invention means to synthesize proteins. In the mentioned term, "foreign" means that the evaluated gene belongs from an organism different than the one used to promote the gene expression.

As used herein, "reporter gene" means a gene whose expression in a bacterial host can be easily monitored or detected. In the context of the present invention, the reporter gene encodes for a green fluorescent protein (GFP) variant.

As used herein, "silent gene" refers to a gene that is unable to express the associated protein from its coding sequence, either during transcription or translation processes in the cellular host.

An embodiment of the invention disclosed herein is directed to the design and development of a synthetic gene (Tn_A), which is an artificial double stranded DNA sequence of 138 base pair (bp) as a result of the specific combination of certain DNA elements. It includes one MuA binding site corresponding to the inverted repeat recognition site for the transposase, one T7 promoter sequence that allows the specific interaction by the T7RNAP, and the following flanking recognition sites for restriction endonucleases: EcoRI, BglII, AscI and BamHI. The design of the mention synthetic gene was intended to locate the MuA binding site and the T7 promoter in different DNA strands (FIG. 1), in order to achieve the desired activity in the final transposon construction.

In one embodiment, the present invention includes pUC57_Tn plasmid, corresponding to an artificial vector of 2,795 pb that can be maintained in a bacterial host cell, and where said plasmid is the result of specific combination of certain DNA elements (FIG. 2). pUC57_Tn has a vector backbone with the ColE1/pMB1/pBR322/pUC origin of replication and an ampicillin resistance gene as a selectable marker after transformation in the bacterial host. pUC57_Tn is the result of cloning Tn_A synthetic gene in the unique EcoRI and BamHI sites, after the enzyme restriction treatment of both the vector backbone and the synthetic gene. Therefore, pUC57_Tn vector in the present embodiment includes one T7 outward-reading promoter and one MuA transposase inverted repeat recognition site, both in a specific manner.

An embodiment of the invention includes pUC57_Tn_kanAB plasmid, which is an artificial vector with a total length of 3,983 bp that can be replicated episomally in a bacterial host cell. pUC57_Tn_kanAB plasmid results from the combination of certain DNA elements (FIG. 3), as it includes the mentioned DNA regions of pUC57_Tn plus an additional resistance gene. In the present invention, pUC57_Tn_kanAB plasmid is the result of cloning the kanamycin resistance gene including both its promoter and transcriptional terminator signals into AscI and BamHI restriction sites of pUC57_Tn. For the current embodiment, the kanamycin resistance gene cloning was performed in an oriented manner in order to ensure an adequate addition of the following DNA regions.

In one embodiment, the present invention is oriented to the development of pBAD18-Cm_t7rnap plasmid (FIG. 4), which is an artificial vector that can be stably maintained in a bacterial host cell. This vector has a total size of 8,738 bp and results after combining the following DNA elements: a ColE1/pMB1/pBR322/pUC origin of replication, a chloramphenicol resistance gene and the T7RNAP coding sequence cloned in the unique KpnI restriction site. Additionally, pBAD18-Cm_t7rnap described in this invention has the T7RNA coding sequence located downstream from the inducible-arabinose promoter and upstream of rrnB T1 and T2 transcriptional terminators.

An embodiment of the invention relates to pUC57_Tn_kanAB_t7 plasmid, which is an artificial vector of 7,097 bp (FIG. 6), resulting from the specific combination and orientation of certain DNA elements and can be maintained inside a bacterial host cell. pUC57_Tn_kanAB_t7 plasmid includes the mentioned DNA elements of pUC57_Tn_kanAB, which are a ColE1/pMB1/pBR322/pUC origin of replication, an ampicillin resistance gene, the Tn_A synthetic gene and the kanamycin resistance gene, plus the inducible-arabinose promoter and the T7RNA coding sequence from pBAD18-Cm_t7rnap vector. pUC57_Tn_kanAB_t7 artificial vector specifically results from cloning the inducible-arabinose promoter and the T7RNAP coding sequence in the unique AscI restriction site of pUC57_Tn_kanAB, between the Tn_A and the kanamycin resistance DNA sequences on the artificial vector.

An embodiment of the invention disclosed herein is directed to the development of pUC57_TnC_T7 plasmid (FIG. 7), which is an artificial vector resulting from the specific combination of certain DNA elements and that can be maintained in a bacterial host cell. This artificial vector includes all the structural elements from pUC57_Tn_kanAB_t7 vector plus a second transposon end, denoted here as Tn_B. pUC57_TnC_T7 plasmid has a total length of 7,240 bp and has specifically cloned the Tn_B region in the unique HindIII restriction site of pUC57_Tn_kanAB_t7. As a consequence, pUC57_TnC_T7 artificial vector has two flanking T7 outward-reading promoters, as well as two MuA transposase inverted repeats recognition sites. Therefore, pUC57_TnC_T7 has cloned the complete TnC_T7 transposon sequence, which in turn can be released through BglII restriction enzyme treatment.

In one embodiment the present invention relates to the development of F076_GFP fosmid (FIG. 11), which is an artificial vector comprising 45,619 bp. This vector results from combining in a specific manner a fosmid backbone, a metagenomic DNA insert and the coding sequence of a reporter gene. The fosmid backbone corresponds to commercial vector pCC2FOS (Illumina Inc., San Diego, Calif., USA). The metagenomic insert resulted from random cloning of metagenomic DNA in pCC2FOS. The reporter gene corresponds to the coding sequence of GFP including a ribosome-binding site (RBS), both DNA fragments cloned as a single amplicon in a unique AscI restriction site on the metagenomic insert.

Figure 9:
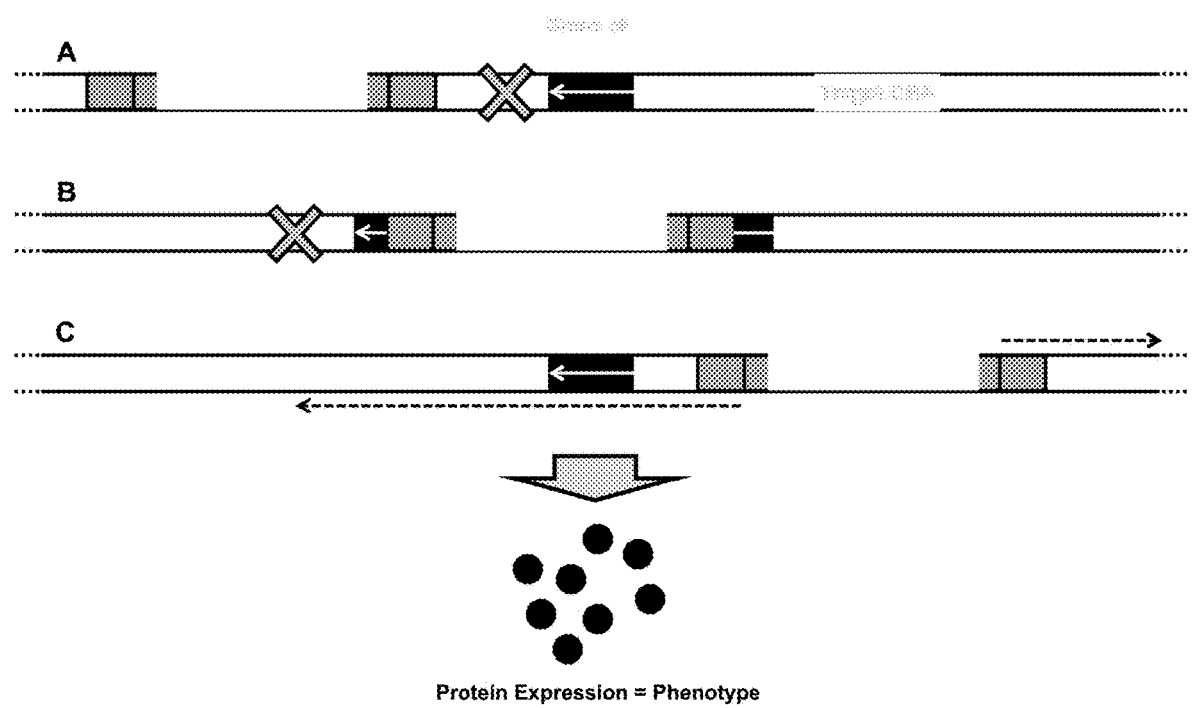
FIG. 9 outlines the principle of the method disclosed herein, directed to enhance DNA transcription as the initial step of foreign gene expression. Specifically, the method comprises the use of transposon TnC_T7, a Mu transposon, to partially supply the transcriptional machinery during functional analysis of genomic/metagenomic libraries. This transposon was conceived and constructed to have the ability to integrate randomly into any episomal DNA, allowing the inducible expression of the adjacent DNA regions in both directions. A, B and C show examples of TnC_T7 transposition events on target DNA and the ability in each case to enhance gene expression as a result of their specific insertion. In case there is a gene of interest (black boxes with white arrows showing reading orientation) in a particular target DNA, the random insertion of TnC_T7 transposon can promote DNA transcription (segmented arrows), which eventually will lead to the expression of particular proteins (black circles) and the detection of the desired phenotype.

An embodiment of the invention disclosed herein is a method to enhance DNA transcription, including, but not limited to foreign gene expression (FIG. 9), which comprises:

(i) Generating DNA libraries based on random transposition or transposon insertions on episomal DNA. The transposition-based DNA libraries can be obtained from purified episomal DNA sequences, like single plasmids, fosmids, cosmids or BACs, having unique DNA inserts, or from pools of episomal DNA sequences each having a different DNA insert.

(ii) Introducing one or more of the said episomal transposition-based DNA libraries of (i) into bacterial host cells by standard transformation methods.

(iii) Inducing the T7RNA polymerase expression in the resulting bacterial isolates transformed with the transposition-based episomal DNA sequences. The specific expression of T7RNA polymerase from each TnC_T7 transposon insertion provides a diverse collection of episomal-derived DNA transcripts or RNA sequences in the resulting bacterial cell population.

(iv) Screening said bacterial host cell population to identify specific bacterial isolates expressing, but not limited to, the reporter gene encoding GFP. Reporter gene expression, as any other phenotype under study using the method disclosed in the present invention, is associated to the specific RNA sequences generated in screened bacteria, which in turn is correlated to specific TnC_T7 transposon insertions on the original episomal DNA libraries.

In one embodiment, the present invention includes eight plasmids corresponding to artificial vectors resulting from random transposon insertions on pKR-C12, a plasmid that includes a silent reporter gene encoding for GFP. The plasmids included in this embodiment are characterized by having only one differential TnC_T7 transposon inserted in the original target plasmid and by having the same length. The specific location of the transposon insertion in each case defines the efficiency of the respective transformed bacterial isolate to express the reporter gene.

EXAMPLES

Example 1: Inducible T7RNAP Expression from $P_{BAD}$ Promoter

Figure 4:
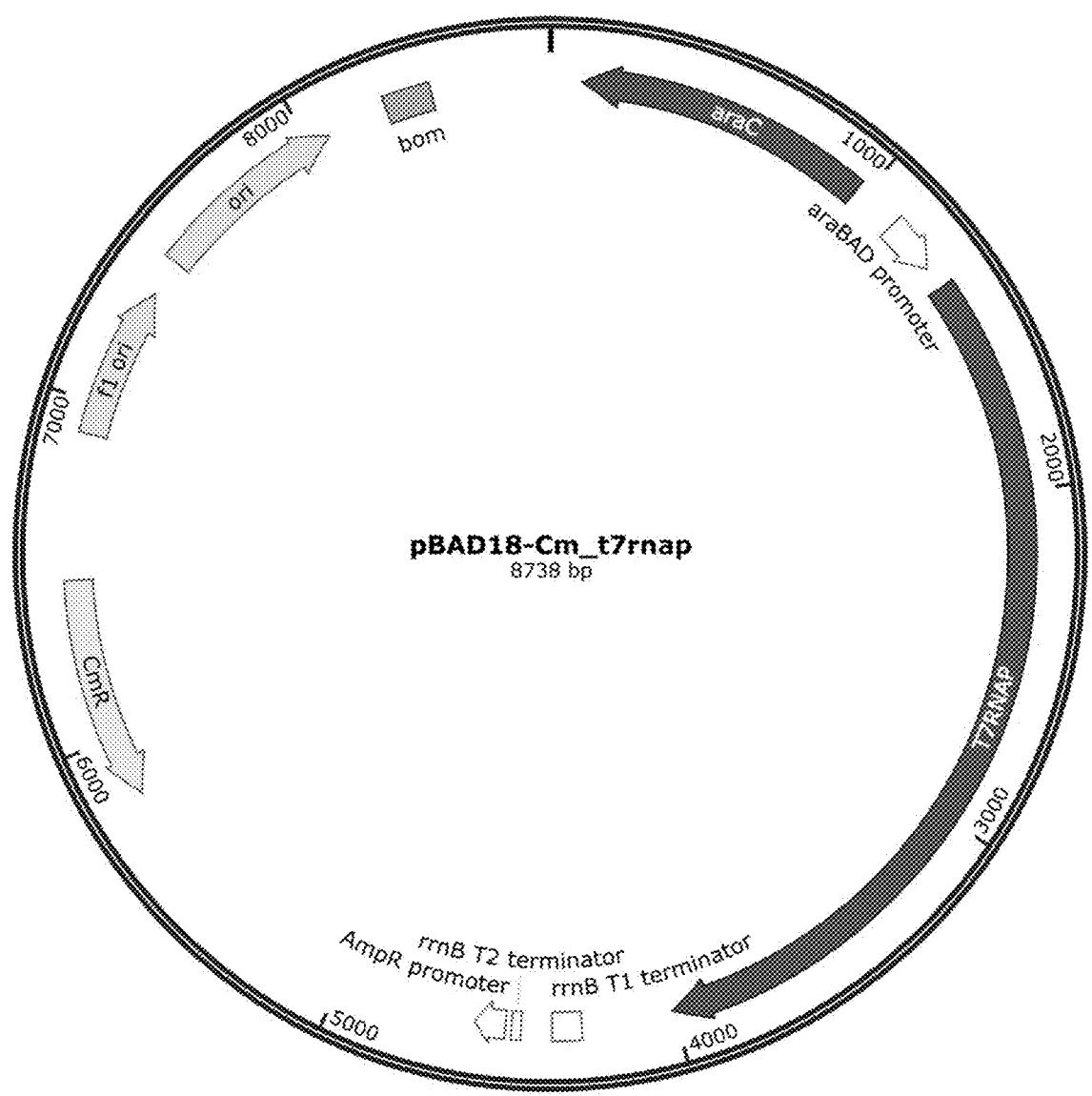
FIG. 4 depicts the cloning of T7RNA polymerase (T7RNAP) coding sequence in the unique KpnI restriction site (post End-Repair) of plasmid pBAD18-Cm (Guzman L M, et al.; *J. Bacteriol*. 1995, 177:4121-30), to generate the pBAD18-Cm_t7rnap plasmid. T7RNAP coding sequence is located downstream of the inducible-arabinose promoter ($P_{BAD}$) and upstream of rrnB T1 and T2 transcriptional terminators. CmR, chloramphenicol resistance gene; f1 ori, f1 bacteriophage origin of replication; ori, high-copy-number ColE1/pMB1/pBR322/pUC origin of replication; bom, basis of mobility region from pBR322; araC, L-arabinose regulatory protein; araBAD promoter, promoter of the L-arabinose operon of *E. coli*.

An artificial vector for the recombinant expression of T7RNAP was generated by cloning its coding sequence in the multiple cloning site of pBAD18-Cm plasmid. For this, T7RNAP coding sequence was amplified with a high fidelity polymerase like Accuzyme (Bioline, London, UK), using purified genomic DNA from E. coli BL21 strain (Invitrogen-Life Technologies, Carlsbad, Calif., USA) as template and the primers provided in Seq-ID1 and Seq-ID2. On the other hand, pBAD18-Cm vector (Guzman L M, et al.; J. Bacteriol. 1995, 177:4121-30) was linearized by KpnI enzyme restriction and its DNA ends repaired with T4 DNA polymerase (New England Biolabs, Ipswich, Mass., USA). Upon purification of both the PCR amplicon and the vector, a ligation reaction and transformation on E. coli TOP10 (Invitrogen-Life Technologies, Carlsbad, Calif., USA) were performed according to standard methods, known in the art. The correct orientation of the insert was verified on plasmid DNA isolated from resulting bacterial clones by restriction enzyme digestion, colony PCR and/or by DNA sequencing of the final construct (FIG. 4).

In a next step, an E. coli TOP10 harboring the pBAD18-Cm_t7rnap was transformed with a plasmid including the coding sequence of peptide AA 9.6 kilodaltons (kDa) located downstream of a T7 promoter (pET28a_AA). Selection of resulting bacterial isolates including both plasmids was done using the corresponding selection markers for both vector backbones.

Figure 5:
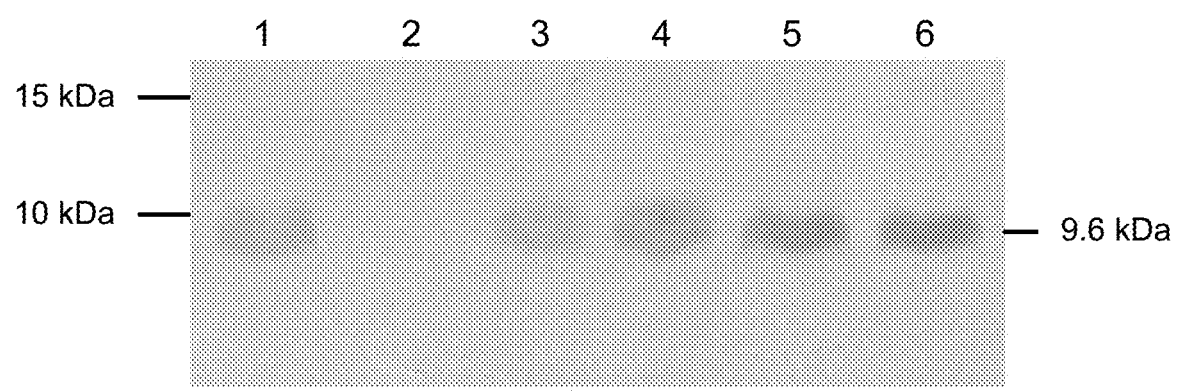
FIG. 5 depicts the detection of AA peptide in a western blot assay, as a result of the expression of T7RNAP derived from different bacterial culture extracts. 1, positive control of AA peptide expression from *E. coli* BL21 DE3 bacterial clone transformed with pET28a_AA plasmid and supplemented with kanamycin and IPTG; 2, *E. coli* TOP10 bacterial clone transformed with pET28a_AA and pBAD18-Cm_t7rnap plasmids and supplemented with kanamycin, chloramphenicol and D-glucose; 3-6, *E. coli* TOP10 bacterial clones transformed with pET28a_AA and pBAD18-Cm_t7rnap plasmids and supplemented with kanamycin, chloramphenicol and L-arabinose.

To assess the expression of the T7RNAP coding sequence from the $P_{BAD}$ promoter of pBAD18-Cm_t7rnap vector, bacterial cell culture was induced with Isopropyl β-D-1-thiogalactopyranoside (IPTG) or L-arabinose, depending on the final receptor host of the mentioned plasmids (either E. coli BL21 or E. coli TOP10, respectively). Detection of peptide AA by anti-poly-Histidine antibodies in western blot assays was performed using whole bacterial extracts, showing in which conditions the T7RNAP can be successfully expressed (FIG. 5).

Example 2: Instruction for Cloning TnC_T7 Transposon Sequence

Figure 1:
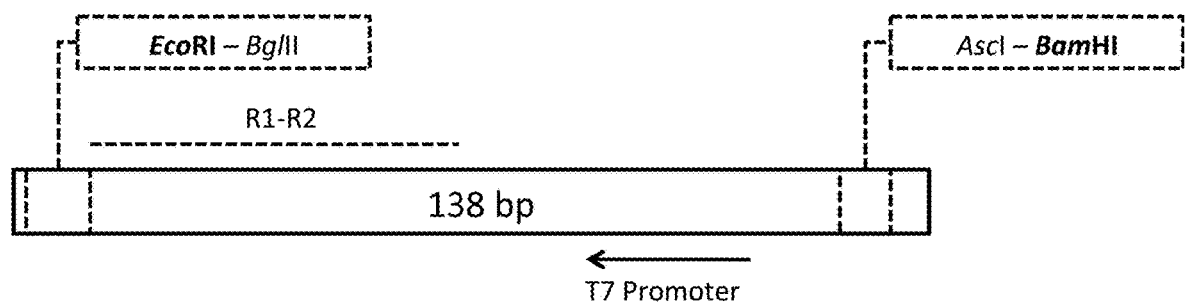
FIG. 1 depicts the structure of the Tn_A DNA sequence, which comprises the R1-R2 MuA transposase-binding sequence, corresponding to one of the inverted repeat recognition sites, and the T7 promoter region in the same DNA molecule, but in the opposite strand. The length of Tn_A gene is of 138 bp and includes flanking recognition sites for the following restriction endonucleases: EcoRI, BglII, AscI and BamHI.
Figure 2:
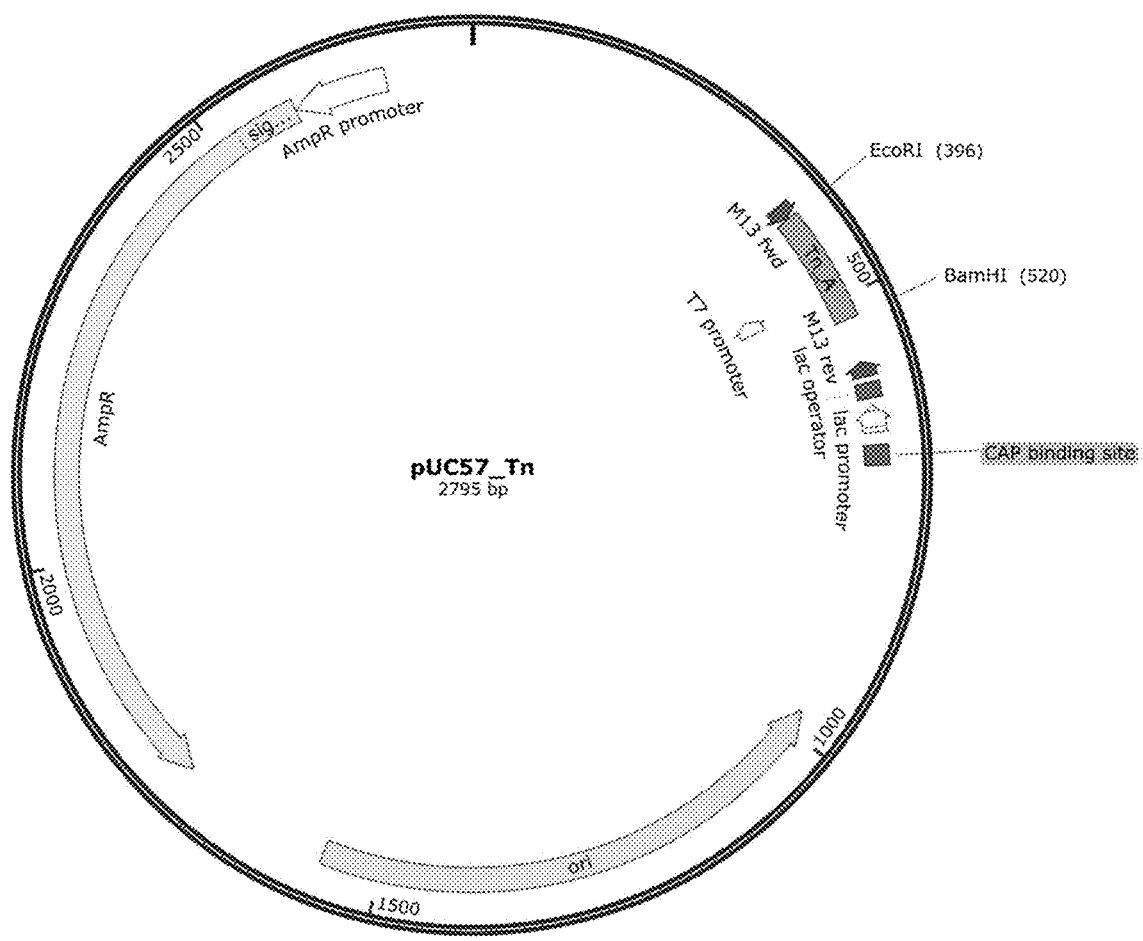
FIG. 2 outlines the cloning of Tn_A DNA sequence in pUC57 vector, to generate pUC57_Tn plasmid. Direct cloning was achieved using EcoRI and BamHI restriction sites in both the gene and in pUC57 plasmid, as a requirement for the subsequent steps in order to construct the plasmid harboring the TnC_T7 transposon. AmpR, ampicillin resistance gene; M13 fwd, annealing site for M13 forward primer; M13 rev, annealing site for M13 reverse primer; ori, high-copy-number ColE1/pMB1/pBR322/pUC origin of replication; CAP binding site, catabolite activator protein binding site.

In order to build the plasmid harboring the complete TnC_T7 transposon sequence, the following steps were performed:

Seq-ID3 was engineered to include the R1-R2 MuA transposase-binding site, one T7 promoter region and EcoRI, BglII, AscI and BamHI restriction enzyme sites (FIG. 1). The resulting DNA sequence was synthesized (Genscript, Piscataway, N.J., USA) and subsequently cloned in the unique EcoRI and BamHI restriction sites of pUC57 plasmid. The correct orientation of Tn_A insertion was verified by restriction enzyme digestions and/or DNA sequencing. The resulting plasmid is denoted here as pUC57_Tn and is provided in Seq-ID4 (FIG. 2).

The kanamycin resistance gene, including its promoter, was amplified by PCR in two independent amplification reactions from pKD4 plasmid (Datsenko K A, et al.; Proc. Natl. Acad. Sci. U.S.A 2000, 97:6640-5). In order to replace the BglII restriction site in the assembled DNA sequence, the resulting amplified fragments from the kanamycin resistance gene were ligated after enzyme digestion with SpeI. The resulting antibiotic resistance gene sequence is provided in Seq-ID5 (SpeI restriction site is shown underlined).

Figure 3:
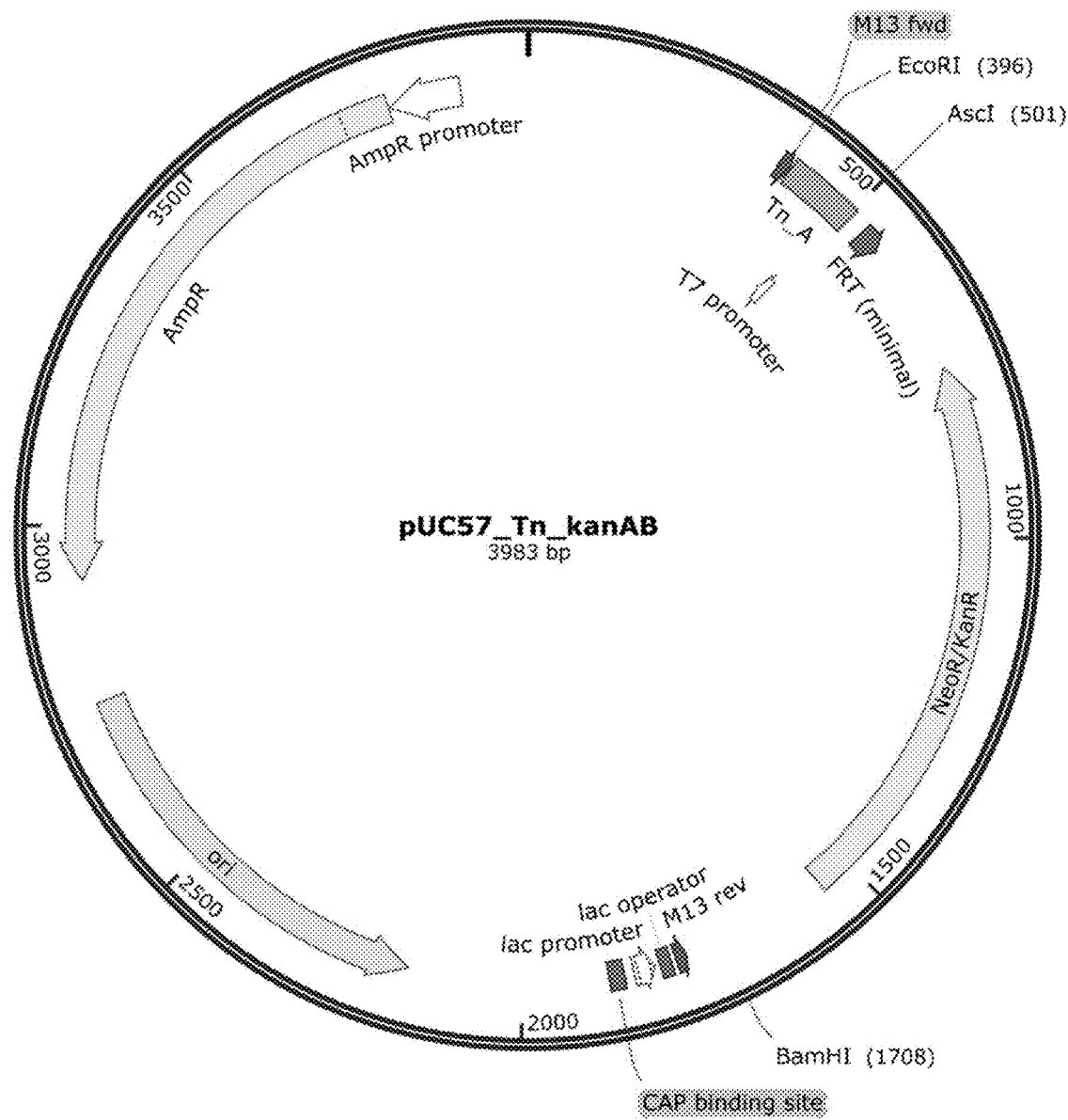
FIG. 3 depicts the cloning of the kanamycin resistance gene (Kan) including its promoter in pUC57_Tn, to generate the pUC57_Tn_kanAB plasmid. Kan was first amplified in two steps, in order to replace the BglII restriction site for SpeI. The ligated product was inserted into AscI and BamHI restriction sites of pUC57_Tn. AmpR, ampicillin resistance gene; M13 fwd, annealing site for M13 forward primer; M13 rev, annealing site for M13 reverse primer; ori, high-copy-number ColE1/pMB1/pBR322/pUC origin of replication; CAP binding site, catabolite activator protein binding site; NeoR/KanR, neomycin and kanamycin resistance gene; FRT, FLP-mediated excision but not integration site.

The 1,214 bp sequence provided in Seq-ID5 was digested with AscI and BamHI, purified and then cloned in pUC57_Tn (Seq-ID4), after digesting the vector with the same restriction enzymes. The correct orientation of the insert was verified on plasmid DNA isolated from resulting bacterial clones by restriction enzyme digestion, colony PCR and/or by DNA sequencing of the final construct, denoted here as the pUC57_Tn_kanAB vector (FIG. 3).

Figure 6:
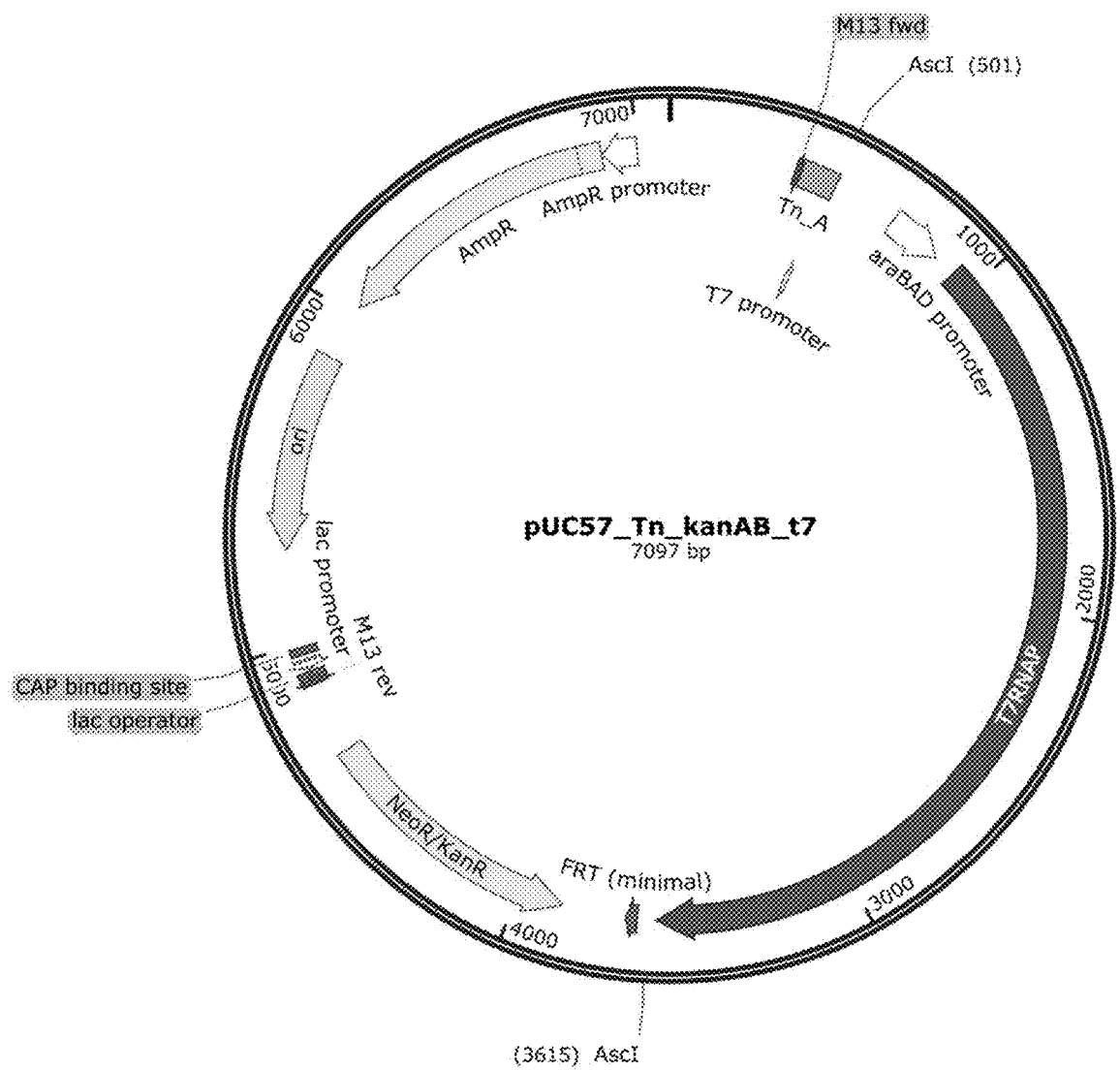
FIG. 6 outlines the cloning of both the inducible-arabinose promoter and the T7RNAP coding sequence, as a single amplicon, in the unique AscI restriction site of pUC57_Tn_kanAB, generating pUC57_Tn_kanAB_t7 plasmid. The $P_{BAD}$_T7RNAP amplicon is located between the Tn_A and the kanamycin resistance DNA sequences. AmpR, ampicillin resistance gene; M13 fwd, annealing site for M13 forward primer; M13 rev, annealing site for M13 reverse primer; ori, high-copy-number ColE1/pMB1/pBR322/pUC origin of replication; CAP binding site, catabolite activator protein binding site; NeoR/KanR, neomycin and kanamycin resistance gene; FRT, FLP-mediated excision but not integration site; T7RNAP, T7RNA polymerase coding sequence; araBAD promoter, promoter of the L-arabinose operon of *E. coli*.

The T7RNAP coding sequence and the inducible-arabinose promoter were amplified with a high fidelity polymerase like Accuzyme (Bioline, London, UK), using purified pBAD18-Cm_t7rnap plasmid DNA (FIG. 4) as template and the primers provided in Seq-ID6 and Seq-ID7 (AscI restriction sites are shown underlined and not additional nucleotides were included on primer sequences to allow for proper restriction enzyme digestion on resulting PCR product). The amplicon of 3,122 bp, corresponding to $P_{BAD}$_T7RNAP sequence (Seq-ID8), was inserted in the unique AscI restriction site of pUC57_Tn_kanAB (FIG. 3), generating pUC57_Tn_kanAB_t7 plasmid (FIG. 6). The accurate orientation of the insert was verified by restriction enzyme digestion, colony PCR and/or by DNA sequencing, on plasmid DNA isolated from resulting bacterial clones transformed with the corresponding ligation reaction.

Figure 7:
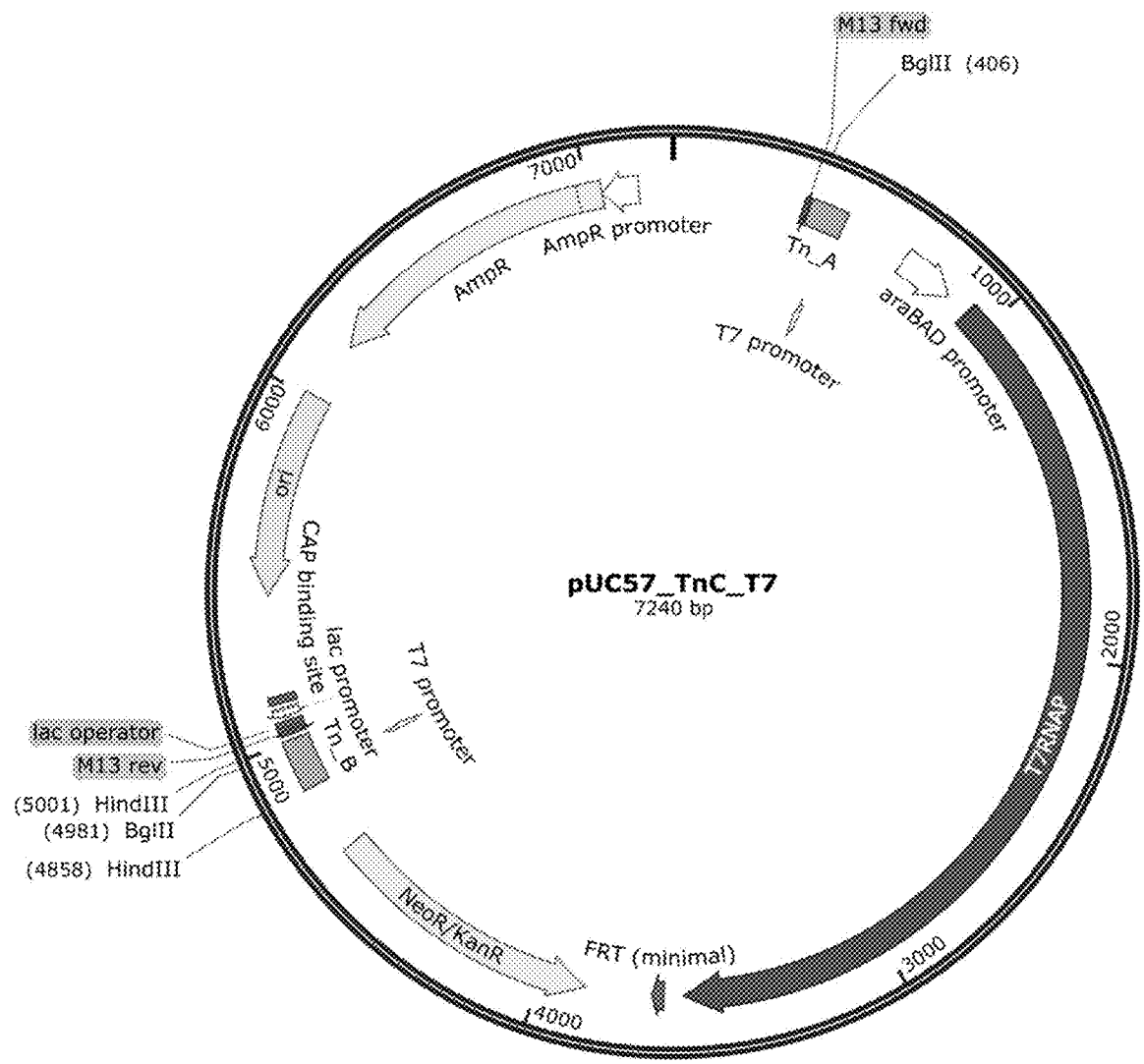
FIG. 7 outlines the cloning of the second transposon end (Tn_B) in pUC57_Tn_kanAB_t7, to generate the pUC57_TnC_T7 plasmid. Tn_B included the other R1-R2 MuA transposase-binding site, the second T7 promoter region of the final TnC_T7 transposon construction and two flanking HindIII restriction sites that allowed its cloning in the target vector. It is also highlighted the BglII restriction sites that are needed to release the TnC_T7 transposon from the plasmid. AmpR, ampicillin resistance gene; M13 fwd, annealing site for M13 forward primer; M13 rev, annealing site for M13 reverse primer; ori, high-copy-number ColE1/pMB1/pBR322/pUC origin of replication; CAP binding site, catabolite activator protein binding site; NeoR/KanR, neomycin and kanamycin resistance gene; FRT, FLP-mediated excision but not integration site; T7RNAP, T7RNA polymerase coding sequence; araBAD promoter, promoter of the L-arabinose operon of *E. coli*.

The cloning of the second transposon end, denoted here as Tn_B, was performed on pUC57_Tn_kanAB_t7 vector (FIG. 6) to generate pUC57_TnC_T7 plasmid (FIG. 7). Tn_B was amplified by PCR with a high fidelity polymerase (Bioline, London, UK), using pUC57_Tn plasmid DNA (FIG. 2) as template and the primers provided in Seq-ID9 and Seq-ID10 (HindIII restriction sites are shown underlined and 3 additional nucleotides on primer 5' ends were included to allow for proper restriction enzyme digestion on resulting PCR product). The 155 bp Tn_B amplicon (Seq-ID11) and pUC57_Tn_kanAB_t7 plasmid were ligated after enzyme digestion with HindIII. The correct orientation of Tn_B insertion was verified by diagnostic restriction enzyme digestion and/or DNA sequencing.

Figure 8:
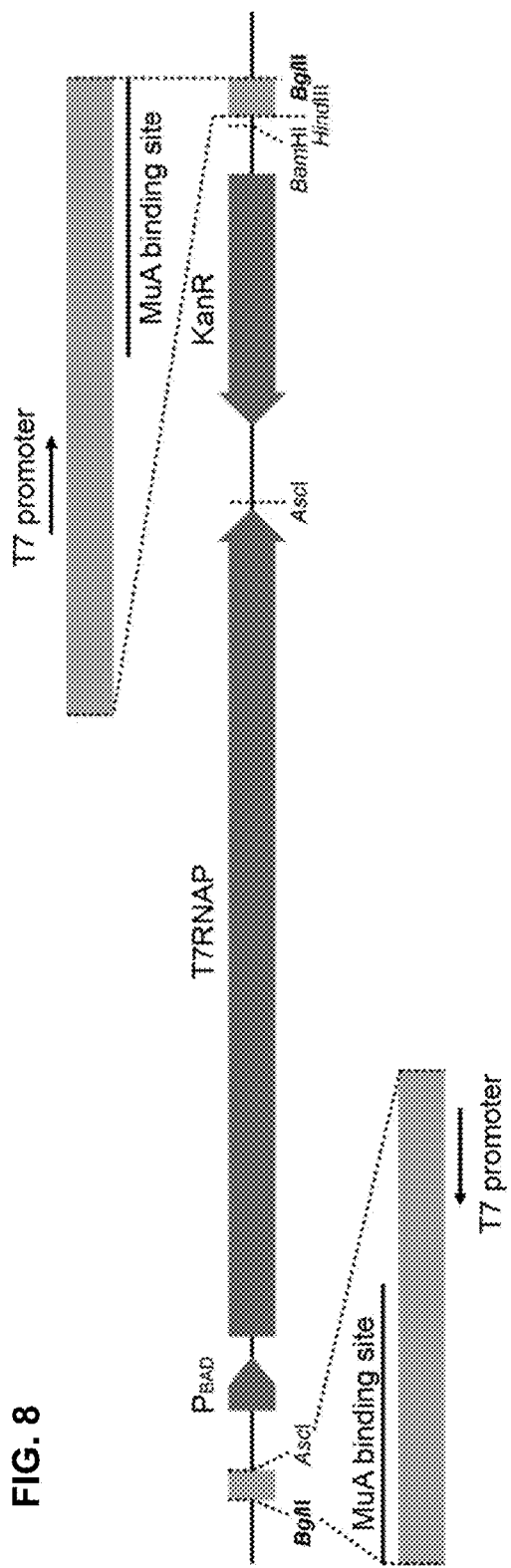
FIG. 8 depicts the scaled structural regions of TnC_T7 transposon. Each of the two MuA transposase binding sites is adjacent to an individual T7 promoter. Italics highlight the most representative restriction sites in the construction of the transposon. The distance between the two BglII restriction sites is 4,575 bp. KanR, kanamycin resistance gene; araBAD promoter (inducible-arabinose promoter ($P_{BAD}$)), promoter of the L-arabinose operon of *E. coli*; T7RNAP, T7RNA polymerase coding sequence.

As a result, pUC57_TnC_T7 plasmid harbors the TnC_T7 transposon, which in consequence includes two flanking R1-R2 MuA transposase-binding sites, two T7 promoter regions, the kanamycin resistance gene and the T7RNAP coding sequence under the regulation of $P_{BAD}$ promoter (FIG. 8). The final design of pUC57_TnC_T7 plasmid can release the transposon by BglII restriction, making it ready for in vitro reactions with the MuA transposase and any episomal target DNA. Performing this enzyme restriction with BglII shown to be crucial in order to generate the required nucleotide 5'-overhangs for an efficient Mu transpososome core assembly and stability, as well as for the strand-transfer reactions (Savilahti H, et al.; *EMBO J.* 1995, 14:4893-903).

Example 3: Identification of Bacterial Cells Expressing GFP as a Result of TnC_T7 Transposition in Plasmid DNA To assess whether the TnC_T7 transposon could enhance the expression of genes in episomal DNA, transposition events with TnC_T7 transposon were performed on pKR-C12 sensor plasmid (Riedel K, et al.; *Microbiology.* 2001, 147:3249-62), which is unable to express GFP in *E. coli* because this bacterial host lacks the quorum sensing system needed for its expression (Riedel K, et al.; *Microbiology.* 2001, 147:3249-62). Therefore, expression of GFP from pKR-C12 in *E. coli* is only possible if transcription process starts from any of the T7 promoters provided by TnC_T7.

Purified pKR-C12 plasmid was used as episomal DNA target for in vitro TnC_T7 transposition reactions with the MuA transposase enzyme (Thermo Scientific, Waltham, Mass., USA), following the manufacturer's recommendations. Resulting reactions were transformed into *E. coli* Epi300 bacterial strain (Illumina Inc., San Diego, Calif., USA), according to standard methods known in the art and using gentamicin and kanamycin as selection markers.

Figure 10:
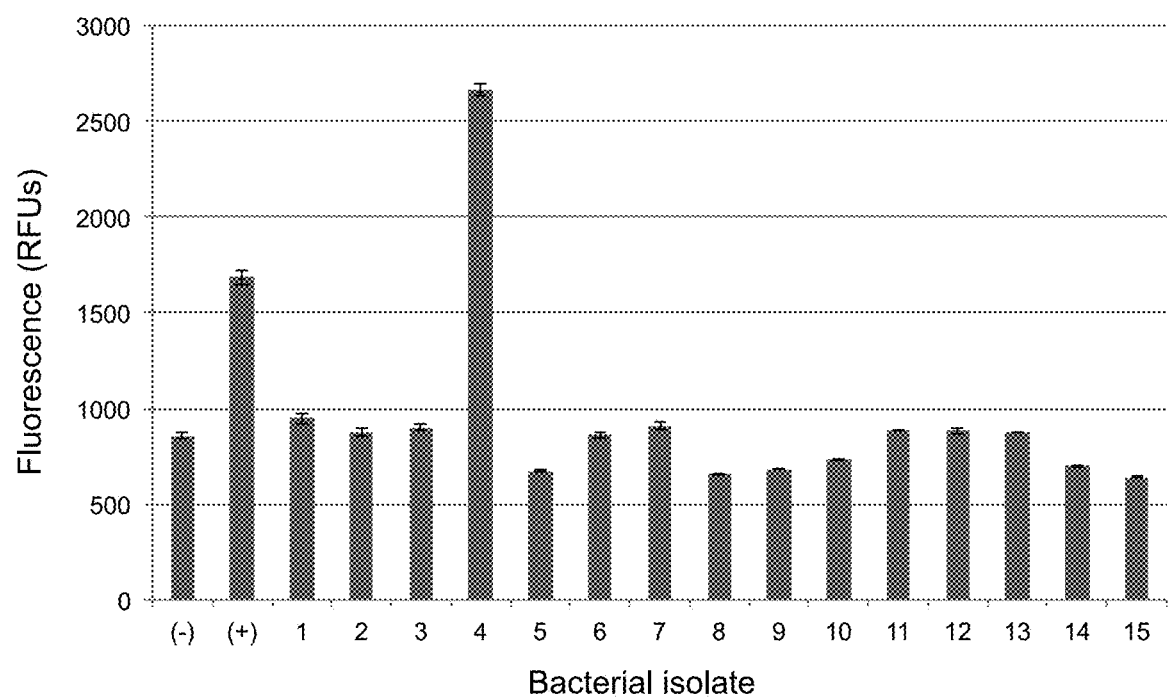
FIG. 10 depicts the initial detection of bacterial clones expressing GFP, based on the random insertion of TnC_T7 transposon in pKR-C12 (1-15). Fluorescence detection is achieved by spectrophotometry and expressed in terms of Relative Fluorescence Units (RFUs). As negative (−) and positive (+) fluorescence controls *E. coli* Epi300 pKR-C12 is incubated in absence and presence of 5 µM N-(3-oxodo-decanoyl)-l-homoserine lactone (3-oxo-C12-HSL) (Sigma-Aldrich, Saint Louis, Mo., USA), respectively.

TnC_T7 post-transposition clones of *E. coli* Epi300 pKR-C12 were grown independently in LB medium until they reached 0.4 Optical Density $(OD)_{600\ nm}$ and induced with 0.2% L-arabinose for 5 additional hours at 30° C. Fluorescence detection assays by spectrophotometry were performed in a Synergy Microplate Reader (BioTek, Winooski, Vt., USA). Each bacterial culture was evaluated in 96-well black polystyrene plates with clear bottom (Sigma-Aldrich, Saint Louis, Mo., USA) and analyzed with an excitation wavelength of 474 nm and emission at 515 nm. As a result of this kind of assays, bacterial clones expressing GFP resulting from TnC_T7 transposition in pKR-C12 were ultimately identified (FIG. 10). Bacterial clones post-transposition were analyzed to localize the TnC_T7 insertion sites on pKR-C12, carrying out Sanger sequencing analysis from primers annealing in the transposon sequence.

Figure 11:
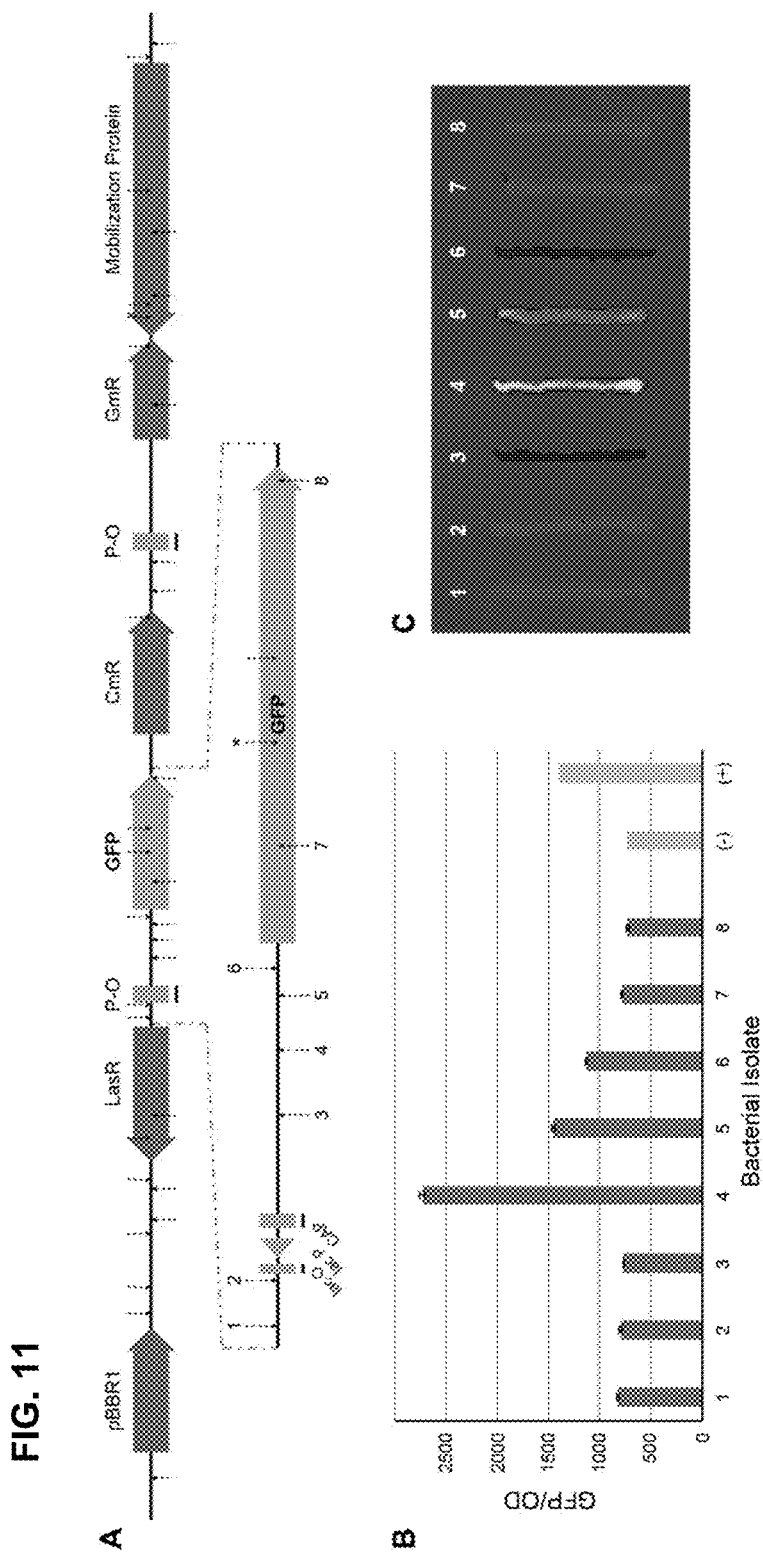
FIG. 11 outlines the TnC_T7 transposon insertions in pKR-C12 and the fluorescence detection of selected bacterial isolates post transposition. A, scale diagram of pKR-C12 plasmid. The plasmid fragment highlighted shows the exact location of the transposon insertions (associated to bacterial clones 1-8) located nearby the GFPmut3* (GFP) coding gene. Segmented arrows oriented from top to bottom represent transposon insertion sites in which t7rnap gene is located in the sense strand of the target DNA, while the arrows from bottom to top represent the same gene located in the antisense DNA strand. pBBR1, replication origin of the plasmid; LasR, transcriptional regulator; P-O, Lac promoter and Lac operator system; GFP, green fluorescent protein; CmR, chloramphenicol resistance gene; GmR, gentamycin resistance gene; CAP, catabolite activator protein binding site; *, two independent TnC_T7 insertions in the same position. B, fluorescence detection by spectrophotometry is expressed in terms of RFUs/Optical Density$_{600\ nm}$ (GFP/OD); 1-8, *E. coli* Epi300 isolates harboring the plasmids with the transposon insertions showed in A; (−), Negative control of GFP expression; (+), Positive control of GFP expression. C, Fluorescence by the IVIS Imaging System detector; 1-8, *E. coli* Epi300 isolates harboring the plasmids with the transposon insertions showed in A.

Alternatively, fluorescence detection assays on bacterial clones post-transposition were achieved after growing bacteria at 37° C. for 14-16 hours in LB-agar plates supplemented with 0.2% arabinose and corresponding selection markers. In this case, GFP expression was assessed using the IVIS 200 in vivo Imaging System (PerkinElmer, Waltham, Mass. USA) with the GFP excitation and emission filters and 15 s of luminescent exposure (FIG. 11).

In consequence, TnC_T7 transposon had the ability to initiate gene transcription in plasmid DNA and its validation as a genetic tool in an *E. coli* strain different than BL21 indicated that T7RNAP expression occurred from its corresponding gene located within the transposon. Resulting plasmids post-transposition in pKR-C12 obtained from bacterial clones 1-8 shown in FIG. 11, exhibited differential GFP expression patterns depending on the specific insertion of TnC_T7 transposon.

Example 4: Instruction for Cloning GFP in Metagenomic Context

Figure 12:
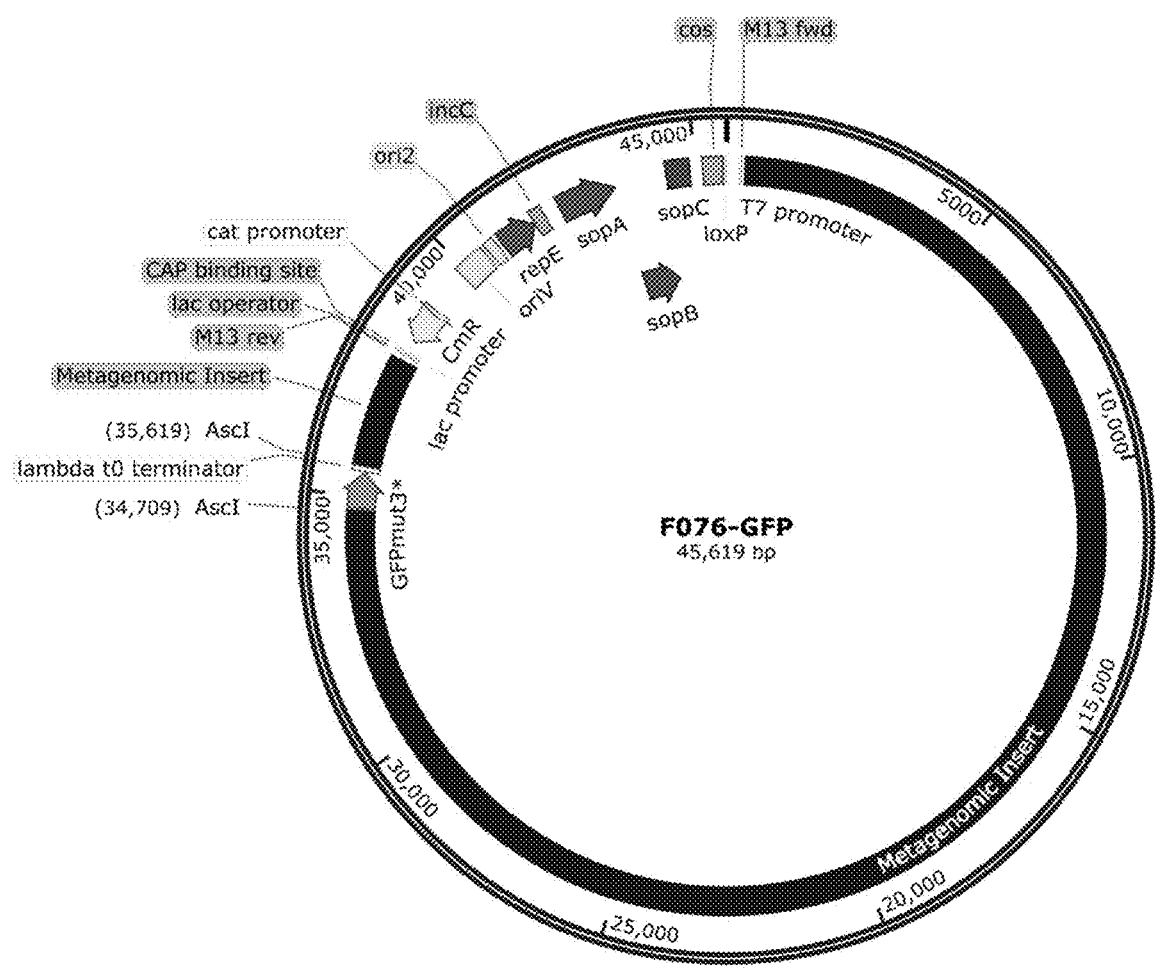
FIG. 12 depicts a derived fosmid from pCC2FOS, which includes a soil metagenomic DNA insert (F076) and where GFPmut3* coding sequence was cloned, to generate fosmid F076_GFP. AscI restriction site was used for cloning GFPmut3* inside the metagenomic insert of F076 fosmid. M13 fwd, annealing site for M13 forward primer; M13 rev, annealing site for M13 reverse primer; CAP binding site, catabolite activator protein binding site; CmR, chloramphenicol resistance gene; oriV, origin of replication for the bacterial F plasmid; ori2, secondary origin of replication for the bacterial F plasmid; repE, replication initiation protein for the bacterial F plasmid; incC, incompatibility region of the bacterial F plasmid; sopA and B, partitioning proteins for the bacterial F plasmid; sopC, centromere-like partitioning region of the bacterial F plasmid; loxP, Cre-mediated recombination site.

A fosmid including the coding sequence of GFP inside its metagenomic DNA insert was generated by cloning the said sequence in a unique restriction site. For this, the GFP coding sequence (denoted also as gfp) including upstream a RBS was amplified with a high fidelity polymerase like Accuzyme (Bioline, London, UK), using purified pKR-C12 plasmid DNA as template and the primers provided in Seq-ID12 and Seq-ID13 (AscI restriction sites are shown underlined and not additional nucleotides would be included on primer sequences to allow for proper restriction enzyme digestion on resulting PCR product). The 918 bp gfp amplicon (Seq-ID14) was introduced inside the DNA insert of a metagenomic clone. For example, purified fosmid DNA from a metagenomic clone harboring a DNA insert belonging to a soil sample was linearized by enzyme restriction and used to insert the gfp amplicon described above. Therefore, the original isolated fosmid DNA, denoted here as pCC2FOS_F076, was digested with AscI restriction enzyme and ligated with the gfp amplicon, to generate F076_GFP fosmid (Seq-ID16; FIG. 12). The accurate orientation of the insert was verified by restriction enzyme digestion, colony PCR and/or by DNA sequencing, on fosmid DNA isolated from resulting bacterial clones transformed with the corresponding ligation reaction.

Example 5: Identification of Bacterial Cells Expressing GFP as a Result of TnC_T7 Transposition in Fosmid DNA To assess TnC_T7 transposon capacity to enhance the expression of genes in fosmid DNA, transposition events were performed on F076_GFP fosmid (FIG. 12). Therefore, purified F076_GFP fosmid was used as episomal DNA target for in vitro TnC_T7 transposition reactions with the MuA transposase enzyme (Thermo Scientific, Waltham, Mass., USA), following the manufacturer's recommendations. Resulting reactions were transformed into *E. coli* Epi300 bacterial strain (Illumina Inc., San Diego, Calif., USA), according to standard methods known in the art, using kanamycin as selection marker.

Figure 13:
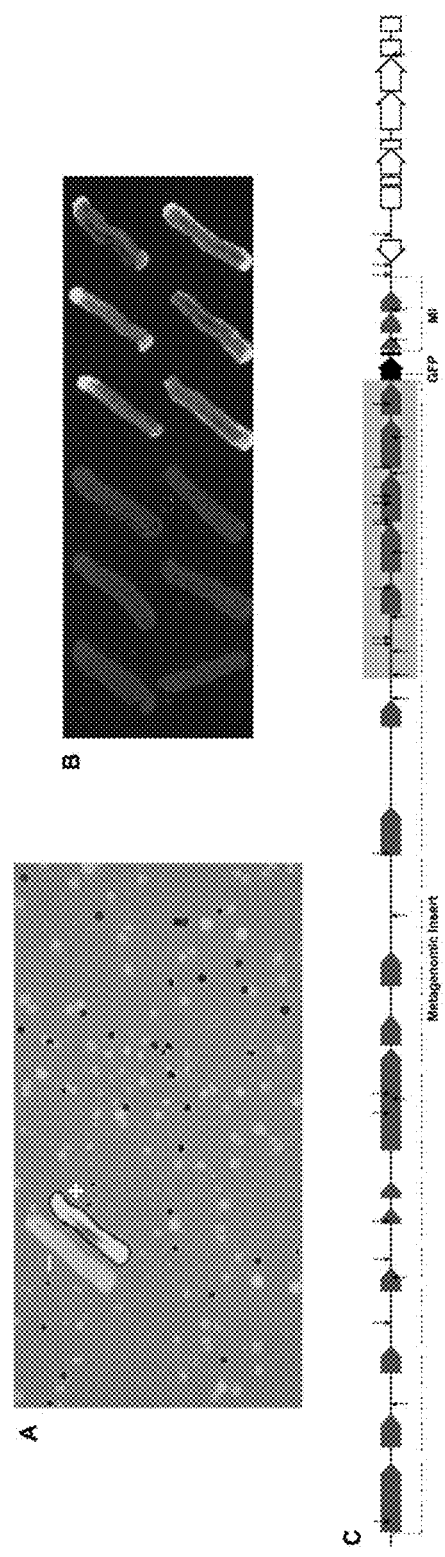
FIG. 13 outlines the fluorescence detection of *E. coli* bacterial isolates transformed with F076_GFP post transposition with TnC_T7 and the location of the transposon insertions along the fosmid sequence. A, fluorescence detection using the Imaging System IVIS for *E. coli* Epi300 isolates transformed with the transposition reaction of TnC_T7 in F076_GFPmut3*. Negative (−) and positive (+) controls of GFP expression were included, corresponding to *E. coli* Epi300 bacterial isolates 2 and 4 from FIG. 11C, respectively. Fluorescence background corrected based on the auto-fluorescence signal of the negative control used. B, re-validation of GFP expression for bacterial isolates with F076_GFPmut3*fosmid using the Imaging System IVIS after their recovery in LB-agar with 20 µg/mL chloramphenicol, 40 µg/mL kanamycin and 0.2% L-arabinose. C, F076_GFPmut3* scale diagram with the identified TnC_T7 transposon insertion sites. GFP, green fluorescent protein coding sequence. White boxes and arrows represent genes and regulatory sequences of pCC2FOS fosmid backbone. Small segmented arrows oriented from top to bottom represent transposon insertion sites in which t7rnap gene is located in the sense strand of the target DNA, while the arrows from bottom to top represent the same gene located in the antisense DNA strand. The Metagenomic Insert (MI) DNA sequence is highlighted, as well as the ORFs with length greater than 150 codons located on the fosmid sense DNA strand. Light-shaded square includes TnC_T7 insertions that promoted GFP expression. CmR, chloramphenicol resistance gene.

Fluorescence detection assays on bacterial clones post-transposition on F076_GFP were performed after growing bacteria at 37° C. for 14-16 hours in LB-agar plates supplemented with 0.2% arabinose and the selection marker. GFP expression was assessed using the IVIS 200 in vivo Imaging System (PerkinElmer, Waltham, Mass. USA) with the GFP excitation and emission filters and 15 s of luminescent exposure (FIG. 13). Sanger sequencing analyses from primers annealing in the transposon sequence were carried out to identify the specific TnC_T7 insertion sites on F076_GFP, from resulting bacterial clones post-transposition. In consequence, validation in the use of TnC_T7 transposon to initiate gene transcription in fosmid DNA was achieved following the proceedings described herein.

Example 6: Identification of Bacterial Cells Expressing Lipolytic Activity as a Result of TnC_T7 Transposition Enhancement of other enzymatic activities different than GFP expression was assessed in metagenomic derived clones using TnC_T7 transposon.

For example, the pCC2FOS_14 gF2 fosmid vector isolated from a metagenomic library constructed with soil-derived DNA was used to detect lipolytic activity, since a potential lipase active site (InterProScan: IPR002168) was identified by in silico analysis on its sequenced metagenomic DNA insert.

Purified pCC2FOS_14 gF2 fosmid was used as episomal DNA target for in vitro TnC_T7 transposition reactions, as described in examples 3 and 5, since functional assays to assess tributyrin degradation in LB-agar media or towards 4-nitrophenyl butyrate (Sigma-Aldrich, Saint Louis, Mo., USA) degradation with the metagenomic clone (harboring pCC2FOS_14 gF2) did not exhibit significant differences compared to the baseline for the negative control of lipolytic activity (*E. coli* Epi300 pCC2FOS).

TnC_T7 transposition reactions on pCC2FOS_14 gF2 were transformed into *E. coli* Epi300 bacterial strain and selected with chloramphenicol and kanamycin. Post-transposition clones were grown independently in LB medium until reaching 0.4 $OD_{600\ nm}$ and induced with 0.2% L-arabinose for 5 additional hours at 37° C. Resulting bacterial cultures were normalized by OD, their respective pellets washed in Tris-HCl buffer and re-suspended in ⅕ of the original volume in Tris buffer. Independent whole bacterial extracts were obtained after cell lysis using a Mini-Beadbeater-96 (Biospec Products, Bartlesville, Okla., USA) and purified by filtration. Following the described methods, functional assays with a set of *E. coli* Epi300 pCC2FOS_14 gF2 clones post-transposition showed significant increases in lipolytic activity by 4-nitrophenyl butyrate degradation (FIG. 11), after quantifying absorbance at 410 nm in a NanoDrop 2000 (Thermo Scientific, Waltham, Mass., USA) (FIG. 14).

The invention claimed is:

1. A transposon "TnC_T7" to partially supply the transcriptional machinery of the host during functional analysis of genomic/metagenomic libraries, the transposon comprising:
   (i) a first flanking MuA transposase inverted repeat recognition site, adjacent to a first flanking T7 promoter reading outwards, the first flanking T7 promoter comprising SEQ ID NO: 3;
   (ii) a kanamycin resistance gene selectable marker, including both its promoter and its transcriptional termination signal, comprising SEQ ID NO: 5;
   (iii) a gene encoding the T7RNA polymerase operably linked to an arabinose inducible promoter ($P_{BAD}$), the gene comprising SEQ ID NO: 8; and
   (iv) a second flanking T7 promoter reading outwards, adjacent to a second flanking MuA transposase inverted repeats recognition site, the second flanking T7 promoter comprising SEQ ID NO: 11.

2. An artificial vector containing following DNA elements:
   a vector backbone having a ColE1/pMB1/pBR322/pUC origin of replication and an ampicillin resistance gene as a selectable marker; and
   (ii) the transposon of claim 1.

3. A method for construction of the transposon according to claim 1, comprising the following steps:
   a) constructing an artificial DNA sequence to locate a MuA binding site and a T7 promoter in different DNA strands, wherein the artificial DNA sequence comprises a first recognition site for restriction endonucleases, one T7 promoter sequence, one MuA transposase inverted repeat recognition site, and a second recognition site for restriction endonucleases,
   wherein the restriction endonucleases for the first recognition site include EcoRI and BglII and the restriction endonucleases for the second recognition site are AscI and BamHI;
   b) constructing a first plasmid comprising a ColE1/pMB1/pBR322/pUC origin of replication, an ampicillin resistance gene as a selectable marker after transformation in the bacterial host and the artificial DNA sequence of step a), wherein said plasmid is constructed by cloning said artificial DNA sequence in a vector backbone having a ColE1/pMB1/pBR322/pUC origin of replication, an ampicillin resistance gene as a selectable marker and a recognition site for restriction endonucleases including HindIII, EcoRI and BamHI, after the enzyme restriction treatment of both the vector backbone and the artificial DNA sequence with restriction endonucleases EcoRI and BamHI;
   c) constructing a second plasmid comprising the mentioned DNA regions of the first plasmid of step b) and an additional resistance gene, wherein said second plasmid is constructed by cloning the additional resistance gene including both its promoter and transcriptional terminator signals into AscI and BamHI restriction sites of the first plasmid of step b), and wherein the additional resistance gene is a kanamycin resistance gene;

d) constructing a third plasmid comprising a ColE1/pMB1/pBR322/pUC origin of replication, a chloramphenicol resistance gene and a T7RNAP coding sequence cloned in the unique Kpnl restriction site, wherein said third plasmid has the T7RNA coding sequence located downstream from the inducible-arabinose promoter and upstream of rrnB T1 and T2 transcriptional terminators;

e) constructing a fourth plasmid, by cloning the inducible-arabinose promoter and the T7RNAP coding sequence amplified from the third plasmid in the unique AscI restriction site of second plasmid between the artificial sequence of step a) and the kanamycin resistance DNA sequences;

f) constructing a fifth plasmid, which comprises all the structural elements from fourth plasmid plus a second transposon end comprising a flanking T7 promoter reading outwards and a flanking MuA transposase inverted repeats recognition site, wherein said second transposon end is specifically cloned in the unique HindIII restriction site; and g) releasing the transposon through BglII restriction enzyme treatment on the fifth plasmid.

4. A method to enhance DNA transcription as the initial step of foreign gene expression, comprising:

generating an episomal transposition DNA library comprising the TnC_T7 transposon of claim 1, wherein said episomal DNA includes plasmids, fosmids, cosmids or BACs, (ii) introducing the episomal transposition DNA library of (i) into host cells, (iii) expressing the T7RNA polymerase encoded from the TnC_T7 transposon, to provide a bacterial host cell population with a diverse collection of episomal-derived DNA transcripts, and (iv) screening said bacterial host cell population to identify bacterial isolates expressing a reporter gene or any other function.

5. A bacterial host cell comprising the artificial vector according to claim 2.

* * * * *

SEQUENCE LISTING

<160> NUMBER OF SEQ ID NOS: 15

<210> SEQ ID NO 1
<211> LENGTH: 27
<212> TYPE: DNA
<213> ORGANISM: Artificial Sequence
<220> FEATURE:
<223> OTHER INFORMATION: Primer 1 for T7RNAP coding sequence

<400> SEQUENCE: 1
atagaattct actaactgga agaggca                                    27

<210> SEQ ID NO 2
<211> LENGTH: 28
<212> TYPE: DNA
<213> ORGANISM: artificial
<220> FEATURE:
<223> OTHER INFORMATION: primer 2 for T7RNAP coding sequence

<400> SEQUENCE: 2
atagaattct cgtattgatt tggcgtta                                   28

<210> SEQ ID NO 3
<211> LENGTH: 138
<212> TYPE: DNA
<213> ORGANISM: Bacteriophage Mu

<400> SEQUENCE: 3
aaacggaatt caggaagatc tgaagcggcg cacgaaaaac gcgaaagcgt ttcacgataa    60
atgcgaaaac ggatcgtgtg tctccctata gtgagtcgta ttaagtactg gcgcgcctca   120
tcatcgttcg gatccttc                                                      138

<210> SEQ ID NO 4
<211> LENGTH: 2795
<212> TYPE: DNA
<213> ORGANISM: Artificial Sequence
<220> FEATURE:
<223> OTHER INFORMATION: Plasmid pUC57_Tn with MuA transposase binding
      site

<400> SEQUENCE: 4

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt caggaagatc tgaagcggcg    420
cacgaaaaac gcgaaagcgt ttcacgataa atgcgaaaac ggatcgtgtg tctccctata    480
gtgagtcgta ttaagtactg gcgcgcctca tcatcgttcg gatcccgggc ccgtcgactg    540
cagaggcctg catgcaagct ggcgtaatc atggtcatag ctgtttcctg tgtgaaattg    600
ttatccgctc acaattccac acaacatacg agccggaagc ataaagtgta aagcctgggg    660
tgcctaatga gtgagctaac tcacattaat tgcgttgcgc tcactgcccg ctttccagtc    720
gggaaacctg tcgtgccagc tgcattaatg aatcggccaa cgcgcgggga gaggcggttt    780
gcgtattggg cgctcttccg cttcctcgct cactgactcg ctgcgctcgg tcgttcggct    840
gcggcgagcg gtatcagctc actcaaaggc ggtaatacgg ttatccacag aatcagggga    900
taacgcagga aagaacatgt gagcaaaagg ccagcaaaag gccaggaacc gtaaaaaggc    960
cgcgttgctg gcgttttttcc ataggctccg cccccctgac gagcatcaca aaaatcgacg   1020
ctcaagtcag aggtggcgaa acccgacagg actataaaga taccaggcgt ttccccctgg   1080
aagctccctc gtgcgctctc ctgttccgac cctgccgctt accggatacc tgtccgcctt   1140
tctcccttcg ggaagcgtgg cgctttctca tagctcacgc tgtaggtatc tcagttcggt   1200
gtaggtcgtt cgctccaagc tgggctgtgt gcacgaaccc cccgttcagc ccgaccgctg   1260
cgccttatcc ggtaactatc gtcttgagtc aacccggta agacacgact tatcgccact   1320
ggcagcagcc actggtaaca ggattagcag agcgaggtat gtaggcggtg ctacagagtt   1380
cttgaagtgg tggcctaact acggctacac tagaagaaca gtatttggta tctgcgctct   1440
gctgaagcca gttaccttcg aaaaagagt tggtagctct tgatccggca acaaaccac    1500 cgctggtagc ggtggttttt ttgtttgcaa gcagcagatt acgcgcagaa aaaaggatc    1560 tcaagaagat cctttgatct tttctacggg gtctgacgct cagtggaacg aaaactcacg   1620
ttaagggatt ttggtcatga gattatcaaa aaggatcttc acctagatcc ttttaaatta   1680
aaaatgaagt tttaaatcaa tctaaagtat atatgagtaa acttggtctg acagttacca   1740
atgcttaatc agtgaggcac ctatctcagc gatctgtcta tttcgttcat ccatagttgc   1800
ctgactcccc gtcgtgtaga taactacgat acgggagggc ttaccatctg gccccagtgc   1860
tgcaatgata ccgcgagacc cacgctcacc ggctccagat ttatcagcaa taaaccagcc   1920
agccggaagg gccgagcgca gaagtggtcc tgcaacttta tccgcctcca tccagtctat   1980
```

```
taattgttgc cgggaagcta gagtaagtag ttcgccagtt aatagtttgc gcaacgttgt    2040
tgccattgct acaggcatcg tggtgtcacg ctcgtcgttt ggtatggctt cattcagctc    2100
cggttcccaa cgatcaaggc gagttacatg atcccccatg ttgtgcaaaa aagcggttag    2160
ctccttcggt cctccgatcg ttgtcagaag taagttggcc gcagtgttat cactcatggt    2220
tatggcagca ctgcataatt ctcttactgt catgccatcc gtaagatgct tttctgtgac    2280
tggtgagtac tcaaccaagt cattctgaga atagtgtatg cggcgaccga gttgctcttg    2340
cccggcgtca atacgggata ataccgcgcc acatagcaga actttaaaag tgctcatcat    2400
tggaaaacgt tcttcgggg cgaaaactctc aaggatctta ccgctgttga tccagttc    2460 gatgtaaccc actcgtgcac ccaactgatc ttcagcatct tttactttca ccagcgtttc    2520
tgggtgagca aaaacaggaa ggcaaaatgc cgcaaaaaag gaataagggg cgacacggaa    2580
atgttgaata ctcatactct ccttttttca atattattga agcatttatc agggttattg    2640
tctcatgagc ggatacatat ttgaatgtat ttagaaaaat aaacaaatag gggttccgcg    2700
cacatttccc cgaaaagtgc cacctgacgt ctaagaaacc attattatca tgacattaac    2760
ctataaaaat aggcgtatca cgaggcccttt tcgtc                              2795

<210> SEQ ID NO 5
<211> LENGTH: 1216
<212> TYPE: DNA
<213> ORGANISM: Artificial Sequence
<220> FEATURE:
<223> OTHER INFORMATION: Plasmid pKD4 with kanamycin resistance gene

<400> SEQUENCE: 5
cgggatcctt ttatggacag caagcgaacc ggaattgcca gctggggcgc cctctggtaa      60
ggttgggaag ccctgcaaag taaactggat ggctttcttg ccgccaagga tctgatggcg     120
caggggatca actagtgatc aagagacagg atgaggatcg tttcgcatga ttgaacaaga     180
tggattgcac gcaggttctc cggccgcttg ggtggagagg ctattcggct atgactgggc     240
acaacagaca atcggctgct ctgatgccgc cgtgttccgg ctgtcagcgc aggggcgccc     300
ggttcttttt gtcaagaccg acctgtccgg tgccctgaat gaactgcagg acgaggcagc     360
gcggctatcg tggctggcca cgacgggcgt tccttgcgca gctgtgctcg acgttgtcac     420
tgaagcggga agggactggc tgctattggg cgaagtgccg gggcaggatc tcctgtcatc     480
tcaccttgct cctgccgaga aagtatccat catggctgat gcaatgcggc ggctgcatac     540
gcttgatccg gctacctgcc cattcgacca ccaagcgaaa catcgcatcg agcgagcacg     600
tactcggatg gaagccggtc ttgtcgatca ggatgatctg gacgaagagc atcaggggct     660
cgcgccagcc gaactgttcg ccaggctcaa ggcgcgcatg cccgacggcg aggatctcgt     720
cgtgacccat ggcgatgcct gcttgccgaa tatcatggtg gaaaatggcc gcttttctgg     780
attcatcgac tgtggccggc tgggtgtggc ggaccgctat caggacatag cgttggctac     840
ccgtgatatt gctgaagagc ttggcggcga atgggctgac cgcttcctcg tgctttacgg     900
tatcgccgct cccgattcgc agcgcatcgc cttctatcgc cttcttgacg agttcttctg     960
agcgggactc tggggttcga aatgaccgac caagcgacgc ccaacctgcc atcacgagat    1020
ttcgattcca ccgccgcctt ctatgaaagg ttgggcttcg aatcgttttt ccgggacgcc    1080
ggctggatga tcctccagcg cggggatctc atgctggagt tcttcgccca ccccagcttc    1140
aaaagcgctc tgaagttcct atactttcta gagaatagga acttcggaat aggaactaag    1200
```
gaggatatgg cgcgcc                                                     1216

<210> SEQ ID NO 6
<211> LENGTH: 26
<212> TYPE: DNA
<213> ORGANISM: Artificial Sequence
<220> FEATURE:
<223> OTHER INFORMATION: primer 1 for T7RNAP coding sequence

<400> SEQUENCE: 6
ggcgcgccca ttaaacgagt atcccg                                          26

<210> SEQ ID NO 7
<211> LENGTH: 29
<212> TYPE: DNA
<213> ORGANISM: Artificial Sequence
<220> FEATURE:
<223> OTHER INFORMATION: primer 2 for T7RNAP coding sequence

<400> SEQUENCE: 7
ggcgcgccca tagaattctc gtattgatt                                       29

<210> SEQ ID NO 8
<211> LENGTH: 3122
<212> TYPE: DNA
<213> ORGANISM: Artificial Sequence
<220> FEATURE:
<223> OTHER INFORMATION: plasmid Pbad_T7RNAP

<400> SEQUENCE: 8
ggcgcgccca ttaaacgagt atcccggcag caggggatca ttttgcgctt cagccatact     60
tttcatactc ccgccattca gagaagaaac caattgtcca tattgcatca gacattgccg    120
tcactgcgtc ttttactggc tcttctcgct aaccaaaccg gtaacccgc ttattaaaag     180 cattctgtaa caaagcggga ccaaagccat gacaaaaacg cgtaacaaaa gtgtctataa    240
tcacggcaga aaagtccaca ttgattattt gcacggcgtc acactttgct atgccatagc    300 attttatcc ataagattag cggatcctac ctgacgcttt ttatcgcaac tctctactgt     360
ttctccatac ccgtttttttt gggctagcga attcgagctc ggtacataga attctactaa    420
ctggaagagg cactaaatga acacgattaa catcgctaag aacgacttct ctgacatcga    480
actggctgct atcccgttca acactctggc tgaccattac ggtgagcgtt tagctcgcga    540
acagttggcc cttgagcatg agtcttacga gatgggtgaa gcacgcttcc gcaagatgtt    600
tgagcgtcaa cttaaagctg gtgaggttgc ggataacgct gccgccaagc ctctcatcac    660
taccctactc cctaagatga ttgcacgcat caacgactgg tttgaggaag tgaaagctaa    720
gcgcggcaag cgcccgacag ccttccagtt cctgcaagaa atcaagccgg aagccgtagc    780
gtacatcacc attaagacca ctctggcttg cctaaccagt gctgacaata caaccgttca    840
ggctgtagca agcgcaatcg gtcgggccat tgaggacgag gctcgcttcg gtcgtatccg    900
tgaccttgaa gctaagcact tcaagaaaaa cgttgaggaa caactcaaca agcgcgtagg    960
gcacgtctac aagaaagcat ttatgcaagt tgtcgaggct gacatgctct ctaagggtct    1020
actcggtggc gaggcgtggt cttcgtggca taaggaagac tctattcatg taggagtacg    1080
ctgcatcgag atgctcattg agtcaaccgg aatggttagc ttacaccgcc aaaatgctgg    1140
cgtagtaggt caagactctg agactatcga actcgcacct gaatacgctg aggctatcgc    1200
aacccgtgca ggtgcgctgg ctggcatctc tccgatgttc caaccttgcg tagttcctcc    1260
taagccgtgg actggcatta ctggtggtgg ctattgggct aacggtcgtc gtcctctggc    1320

-continued

```
gctggtgcgt actcacagta agaaagcact gatgcgctac gaagacgttt acatgcctga    1380
ggtgtacaaa gcgattaaca ttgcgcaaaa caccgcatgg aaaatcaaca agaaagtcct    1440
agcggtcgcc aacgtaatca ccaagtggaa gcattgtccg gtcgaggaca tccctgcgat    1500
tgagcgtgaa gaactcccga tgaaaccgga agacatcgac atgaatcctg aggctctcac    1560
cgcgtggaaa cgtgctgccg ctgctgtgta ccgcaaggac aaggctcgca agtctcgccg    1620
tatcagcctt gagttcatgc ttgagcaagc caataagttt gctaaccata aggccatctg    1680
gttcccttac aacatggact ggcgcggtcg tgtttacgct gtgtcaatgt tcaacccgca    1740
aggtaacgat atgaccaaag gactgcttac gctggcgaaa ggtaaaccaa tcggtaagga    1800
aggttactac tggctgaaaa tccacggtgc aaactgtgcg ggtgtcgata aggttccgtt    1860
ccctgagcgc atcaagttca ttgaggaaaa ccacgagaac atcatggctt gcgctaagtc    1920
tccactggag aacacttggt gggctgagca agattctccg ttctgcttcc ttgcgttctg    1980
ctttgagtac gctggggtac agcaccacgg cctgagctat aactgctccc ttccgctggc    2040
gtttgacggg tcttgctctg gcatccagca cttctccgcg atgctccgag atgaggtagg    2100
tggtcgcgcg gttaacttgc ttcctagtga accgttcag gacatctacg ggattgttgc    2160
taagaaagtc aacgagattc tacaagcaga cgcaatcaat gggaccgata acgaagtagt    2220
taccgtgacc gatgagaaca ctggtgaaat ctctgagaaa gtcaagctgg gcactaaggc    2280
actggctggt caatggctgg cttacggtgt tactcgcagt gtgactaagc gttcagtcat    2340
gacgctggct tacgggtcca aagagttcgg cttccgtcaa caagtgctgg aagataccat    2400
tcagccagct attgattccg gcaagggtct gatgttcact cagccgaatc aggctgctgg    2460
atacatggct aagctgattt gggaatctgt gagcgtgacg gtggtagctg cggttgaagc    2520
aatgaactgg cttaagtctg ctgctaagct gctggctgct gaggtcaaag ataagaagac    2580
tggagagatt cttcgcaagc gttgcgctgt gcattgggta actcctgatg gtttccctgt    2640
gtggcaggaa tacaagaagc ctattcagac gcgcttgaac ctgatgttcc tcggtcagtt    2700
ccgcttacag cctaccatta acaccaacaa agatagcgag attgatgcac acaaacagga    2760
gtctggtatc gctcctaact ttgtacacag ccaagacggt agccaccttc gtaagactgt    2820
agtgtgggca cacgagaagt acggaatcga atcttttgca ctgattcacg actccttcgg    2880
taccattccg gctgacgctg cgaacctgtt caaagcagtg cgcgaaacta tggttgacac    2940
atatgagtct tgtgatgtac tggctgattt ctacgaccag ttcgctgacc agttgcacga    3000
gtctcaattg gacaaaatgc cagcacttcc ggctaaaggt aacttgaacc tccgtgacat    3060
cttagagtcg gacttcgcgt tcgcgtaacg ccaaatcaat acgagaattc tatgggcgcg    3120
cc                                                                   3122
```

<210> SEQ ID NO 9
<211> LENGTH: 28
<212> TYPE: DNA
<213> ORGANISM: Artificial Sequence
<220> FEATURE:
<223> OTHER INFORMATION: primer 1 for Tn_B

<400> SEQUENCE: 9
ataaagctta acggaattca ggaagatc                                       28

<210> SEQ ID NO 10
<211> LENGTH: 26
<212> TYPE: DNA

```
<213> ORGANISM: Artificial Sequence
<220> FEATURE:
<223> OTHER INFORMATION: primer 2 for Tn_B

<400> SEQUENCE: 10
ataaagcttg aaggatccga acgatg                                          26

<210> SEQ ID NO 11
<211> LENGTH: 155
<212> TYPE: DNA
<213> ORGANISM: Artificial Sequence
<220> FEATURE:
<223> OTHER INFORMATION: Tn_B amplicon

<400> SEQUENCE: 11
ataaagctta acggaattca ggaagatctg aagcggcgca cgaaaaacgc gaaagcgttt     60
cacgataaat gcgaaaacgg atcgtgtgtc tccctatagt gagtcgtatt aagtactggc    120
gcgcctcatc atcgttcgga tccttcaagc tttat                               155

<210> SEQ ID NO 12
<211> LENGTH: 25
<212> TYPE: DNA
<213> ORGANISM: Artificial Sequence
<220> FEATURE:
<223> OTHER INFORMATION: primer 1 for GFP

<400> SEQUENCE: 12
ggcgcgccag tacttcggcc tgaaa                                           25

<210> SEQ ID NO 13
<211> LENGTH: 26
<212> TYPE: DNA
<213> ORGANISM: Artificial Sequence
<220> FEATURE:
<223> OTHER INFORMATION: primer 2 for GFP

<400> SEQUENCE: 13
ggcgcgccta gctcctgaaa atctcg                                          26

<210> SEQ ID NO 14
<211> LENGTH: 918
<212> TYPE: DNA
<213> ORGANISM: Artificial Sequence
<220> FEATURE:
<223> OTHER INFORMATION: GFP amplicon

<400> SEQUENCE: 14
ggcgcgccag tacttcggcc tgaaaaaacc aggagaactg aacaagcatg cgtaaaggag     60
aagaactttt cactggagtt gtcccaattc ttgttgaatt agatggtgat gttaatgggc    120
acaaattttc tgtcagtgga gagggtgaag gtgatgcaac atacggaaaa cttacccttc    180
aatttatttg cactactgga aaactacctg ttccatggcc aacacttgtc actactttcg    240
gttatggtgt tcaatgcttt gcgagatacc cagatcatat gaaacggcat gactttttca    300
agagtgccat gcccgaaggt tatgtacagg aaagaactat attttttcaaa gatgacggga    360 actacaagac acgtgctgaa gtcaagtttg aaggtgatac ccttgttaat agaatcgagt    420
taaaaggtat tgattttaaa gaagatggaa acattcttgg acacaaattg gaatacaact    480
ataactcaca caatgtatac atcatggcag acaaacaaaa gaatggaatc aaagttaact    540
tcaaaattag acacaacatt gaagatggaa gcgttcaact agcagaccat tatcaacaaa    600
atactccaat tggcgatggc cctgtccttt taccagacaa ccattacctg tccacacaat    660
```

```
ctgcccttt c gaaagatccc aacgaaaaga gagaccacat ggtccttctt gagtttgtaa    720
cagctgctgg gattacacat ggcatggatg aactatacaa ataagcttaa ttagctgagc    780
ttggactcct gttgatagat ccagtaatga cctcagaact ccatctggat tgttcagaa     840 cgctcggttg ccgccgggcg ttttttattg gtgagaatcc aagctagctt ggcgagattt    900
tcaggagcta ggcgcgcc                                                   918
```

<210> SEQ ID NO 15
<211> LENGTH: 45619
<212> TYPE: DNA
<213> ORGANISM: Artificial Sequence
<220> FEATURE:
<223> OTHER INFORMATION: F076_GFP fosmid

<400> SEQUENCE: 15

```
gcggccgcaa ggggttcgcg tcagcgggtg ttggcgggtg tcgggctgg cttaactatg      60 cggcatcaga gcagattgta ctgagagtgc accatatgcg gtgtgaaata ccgcacagat    120
gcgtaaggag aaaataccgc atcaggcgcc attcgccatt cagctgcgca actgttggga    180
agggcgatcg gtgcgggcct cttcgctatt acgccagctg gcgaaagggg gatgtgctgc    240
aaggcgatta agttgggtaa cgccagggtt ttcccagtca cgacgttgta aaacgacggc    300
cagtgaattg taatacgact cactataggg cgaattcgag ctcggtaccc ggggatccca    360
cgtacaacga cacctagacc acatacggat gtgcaactgc agacgatggc ccagttcgcc    420
gtcaactatg tcgatgcgct cgatcgcgat agcgtcgtca caatgttcga atacgacaag    480
aatctgggga atggctggaa cctgggagat aacccgtatc cctatgatcc cacgaatccc    540
actgccatgc agcaggatga cgaccccagc cccggcgtat cgacggagcg cggcgtggta    600
tttggagtgg aagctcagac gctcgccttc agcgaatcgc ttgcgttcat ttgcgacaaa    660
gatccctcta caaattaccc cgccacgact ttcgacgata agcagcagga tcacccttac    720
atcttcattg aattgagcaa tgtcggtcct gccccggtct catggaacaa cggttcgtgg    780
cgcattcgac ggctgggaac caccggtatt cccgccgcgg ataccctgat cgaacgtcgc    840
ttgacgatcc agcaggcatc catcggcgca ggtcagcagt tcacgatcgg cagcggtgac    900
ggtaccgaca catttatgga cggaaacggg gcgacaattt atcgctccag tgacttccgc    960
gtcgactacg atctggacgg aactttcgac cgcatcgttc cgaacattcc cgagtccact   1020
ccgccgacga gtatgcagac acccacgccc gaccccggtt gcgacctcga tctcgtccat   1080
cagcgcgatc agaattactt cacgctgaca acggtgctaa ctcggcagt ctcgcggggt    1140 gggttcctgt acgacagcaa caacccaact atcaagccgg cggtgggtga tggtattacg   1200
ctcgtcctcg agcgtcgcct gcacttaaat cggacggccc ccttatcgag caacaccgcc   1260
gaggaaaacg acaacccgtg gatcgaagtg gaccgtcttg ctccaggcct tggtgccagt   1320
gctggcggtt cagtaccgg cttgatcatg gaatttcagg cttcgatggc ctcagccact    1380
ttgcagcaaa atcttacgaa cctgcagagc accgaacggg tgcagcccct cgatcgaacg   1440
caagcagctc tccatccgac cgcgctcaat gcgaacagca tcgcccaatc gaccccccaac   1500 ggttatggat ggattgccaa ttcgaataca caaacagcct acacgatttg gcagccgcac   1560
ttcgatcgcg atttcgcatc cgttgtcgaa ttgatggctc tcccgctcta tgggcctaat   1620
cagatctatg tgaaccaatc ttcgaatccg caactgacga tgaattcatt gatcaaaatg   1680
gatggcacaa ataccgcagg tacgctgttc ctgaatccaa gctttgccga tgcgaatttc   1740
```

```
tgggccgatt cgttcggcaa ccgctggcat cggctgtttg aaatccttga agttccgccg    1800
cggcccggta agcaagtcgc cgattatctg caacaaacac tgcctcgtac gccaggcagg    1860
ttaaatgtga atatgatccg aaacggtgaa gtgctgggcg cgctcatcga tgacatgaac    1920
cagatcaact ataccgatat gagcgacaac agttcgtttg acggctccaa tcgcaactgg    1980
tgggatcaat tccgtgcggc ccgcgatcag ttcgatccgg cgacgggttt gtatcttccc    2040
ggttccccat catcgcggcc gttcgcgat ttcgcatacg ccaagatca gacgagcagc    2100 ctccagcaca cgctcctgca gacgctgcct tatgacctga gcaacccacc tccggccgga    2160
aatgcccgaa atctcttcga ggcgcgttcg tatagtgata ttggagcgac aaccgattca    2220
acgaagaaca aggtggatta ctacacccgc catcgcctgc tctccaaaat tgtcggaaat    2280
accaccactc gcagcaacgt cttcatggtg tgggcttcgg tgggatattt ccaggccgtc    2340
caaaacaacg acggcagcgt tcaaatcggc ggtgcattaa cgtccagcca gcccgatcac    2400
cggggtttct ttgtcatcga ccgttcgcaa ctcaacagg cgtacaattc acaaaccggg    2460
aagttcgact atcgcaagtt cattcaatac cggcagaccc ttaaatagac aaccccgtag    2520
acaactccgc gaaatcgtgg tgattttttg gcaaaatgtt gttgattttt tgaaggcgtc    2580
aacgtttaac ttctaagctg gcacgaagtg tcaccaccca tcgcatcgtt ttcatgattt    2640
gagcttcgga aatcaggcaa atccctatgc tcaaaatcga aaaaaggtt cgttcttcat    2700 ggttttttca ccacaaaccg gtccaatttg gtcataatga caggagccgt cctgcggcaa    2760
ttccaagaca atcggcagcg catttcagtt ctttagctta aaatacaacc accttcctgg    2820
gctattcgac ctcaagtcaa cccgcggcgt cgggggagaa gcggaaggtt tcgacttcat    2880
cgtgcaacag cgatgagcgg gcaggacaag acgacccacc cccccgaaat ttctggagat    2940
taagacatga gagcttttca gattcgtaaa ccccgttcgg cccgccgagg gttcaccctc    3000
atcgaactgc tcgtggtgat ctcgatcatc gccaccctga ttgcgttgct gaccccgcc    3060 gtccaaagtg ctcgtgctgc cgcacgccgc ttgcaatgcc tcaacaacat gaagcaaatg    3120
tgcctggcgt taaccaacgc ctccaccagt agaaatggcc agctcccgcc gctcgtggat    3180
gacttcaacg gaactggtta cggttggccg gcgtcgatcc tcggttacgt cgatcgtgcc    3240
gacatcgtca ataacgggtt ggtcggaacg aatctcggtt tgtcgattag tgtttttacc    3300
tgccccgatg atattaacaa cttccgtcaa cctggtggtt tgagctacgt cgcgaatgct    3360
ggctatggtg ccttcactgt tacgtctgga gttatcactg aaaccggcgg aaccggcaag    3420
cacacggggt ataatatcga ctgggatcag tctgccgcgc tcggatcgcc cgattacgat    3480
attgctcatg acacgggtgc gatgtggcgt gcaactgtca ataacttccg gatgacgctc    3540
gatcggatcg ggggacgcga tggactgtca caaacctatc tcctcagcga aaatatcaat    3600
gctggcagca gcaccggttg gtcatccaac gacctgcgcc agattgcttt cgtgttggat    3660
gcggcttgta ccactggtcc cccgcttaca ccaacctatt tcggtacttc cgcgggagcc    3720
ttggctccga atgggttgtt attggcgaat ttcaagccca atttcaatac cacgggaacg    3780
ttgcgcggca cttcgcctgt ccccagttcg ttgcacccgg aatcgtcat catgggtttc    3840 tgtgatggcc atgcgtcgcc ggttaacgag tccattgaca ccacaattta tgcactgcag    3900
atgtcttcgg gtggtgtgcg tcttggtcag cgtccgttgg gcgacaacga aatttagagc    3960
cgttcacttc ctgacgagaa cgtgattacg aaaacaaaag cccacggggtt acaacccgtg    4020 ggcttttttcg ttggagcctg accacaacga gaatgctcgt ggtgatgtgg gcgaattcag    4080
agagattggc ctcaattacc cctcaattgc gcgctgtatc acatgaattg cgctcgaatt    4140
```

```
gcgctgtatt acgtggaagc gaaaaagcgg tggttatggg ctgtatccca ttattttgta    4200
gtgagttacg aagaatgggt tccgaaaacc agcgatgctg cgaatcttcg cgtcctgtag    4260
ggacaacaga tcgatgtgtc gcgtaaccaa ttgacacaac ggaggatgcg ttgccttcgc    4320
atgggcttcg cagtggggcg cgaaaacacg agttgtctcg cgttagcaat ccctgtactt    4380
agcaaaaacg gggtcaattg caccccgata agatcgggtt aatcccccttc aaactgcacc    4440 aggcagtgca ggtcgaagcg cgagagcttt ttgcggccgc ccagggatgg gagttcgatc    4500
acgaaggcgc aacccacgac gaggcctccc aggcgttcga cgatctggca ggtggcgagt    4560
gacgtgccgc cggtggcgag caggtcgtcg acgatcaggc agcgttcgcc ggccttgatg    4620
gcgtctttgt ggatctcgat gcagtcggtg ccgtattcaa gcgagtattc ctgccgttcg    4680
acgtggtaag gcagcttccc cttttttgcgg gccatcacca tgccgcaatg caggtgatgg    4740
gcgagcgccc cgccgacgac gaaccccccgc gattcaatcg cgatcaccttt gtcgatcggc    4800 gagtatttgt aatgcgagac gaattcgtca atcgcatgct tgaaccccca ggcatcctgc    4860
agcagcgtcg tgatgtcgcg gaactgaatt ccgggcttcg gaaagtcggg aatcgtgcgg    4920
atgagggatt tgagatgttc cattgtgggc gatttgaaga tagaggattg aggagggaag    4980
attgccacgt ttcgcgcggt taacgaagtt gctgctttag gttttccaag tacggtggcc    5040
ggatgattcc tttttcggtg atgaaggcgg cgatcaggtc ggccggtgtt acgtcgaagg    5100
ctgggttata gacgggaatg ccatccggtg caatctgacg tcccattcca tgcgtgattt    5160
cgcgcgggtc gcgctgctcg atggggattt ccttcccgct cgccagcgac aggtcgaacg    5220
tgctggccgg ggcggccaca taaaacggaa tcttatgata agccgccgac acggccacgc    5280
catacgtgcc gattttgttc gccgcgtcgc cattggcaac gatgcgatcg gctccgacga    5340
cgacggcctg tacgcgtcct tcgcgcatca cctgggctgc catcgaatcg cagatcagcg    5400
tggcatcgag cccccgttgt tgcagttccc acgcagtcag ccgggcaccc tgcagcagcg    5460
gccgcgtttc atcggcgaat acgtgcagcc gtttgcctgc ttcgtgagca gcgaaaaaga    5520
cggccaatgc cgtcccgtag tcggccgtcg ccagtccccc cgcgttgcaa tgcgtcagca    5580 cccccttgtcc atccgtcaga agttctgcac cgtaacgccc aatcgcccgg cacgtctgcc    5640
gatcttcttc cgcgatcgtg tgcgcttctg cgagcaaccg cccggcaatc tcatcggcgg    5700
tgtatcgccc gcgcagatcg acagccacgc gctgcatgcg ctcgagcgcc agaacaggt    5760 tgacggccgt tggtctgctc gtcgccaggt agccgcacac ttcctgcagc cgctggaaaa    5820
acgcctcttc gttttgcccg cggacagtct gcattcccag gcagacgcca tacgccgccg    5880
cgatgccgat ggcggggggcg ccgcgcacgc gcagcatacg aatcgcctcc cacaacgttt    5940
cgacatcagg gcagacgatc tcgatgaatt ccaacggtaa cagcgtttga tcgatgagga    6000
cgagtttccc ggccgtgtcc ccttcccagt gcagcgtggg agtttgccag cgattggaat    6060
tgggagagtg catgtgtctg acgctatcca caagttgatg ggttgctaat gacttgagtc    6120
tagttgcgct ttcagccagg tatagactga gtcgccgatt tgcagataac cgggttcgct    6180
cgggtgtgct ccattgttga gcctcgttcc tttgacgtcg gttcgtccgt tccaggggc    6240 ttcggttgcg gggtagttgt gcacgcaatc gatgttgatg tacgtcggaa ccatgtggag    6300
gaattcctga tcgcggttgc cgtacttctc gagcatgcgt tccacgagcc gatgttgatt    6360
gcgcttgtat tgccagcggg tctgtccggt tttgtaattc gccccaaatg cgtcttgcgt    6420
cgccgccggg gggatcggca acataacgcc gatgcgcgtt tctttttca aaccgtgaat    6480
```

```
catctcgatg agttgatcgt agtgtttgag catcacatcg atccctgtt cgacgttttc    6540
gtccgtgagc gagaatgtgt cgttcgggcc gaggaagatg gtgacgaaat cggggggctg   6600
tccgtcattg tactctttgc agtaacgcgg aagtcgata gtcttggtgc cgtccgggtt    6660
caagtagata aacgggctgc ctcgttttcc atgatcgggg tccttgcggg ccgtctcgct   6720
gtagaaggtg gcaaaccgca acgcggtcca accgccgtaa ccttcgtgcc ggacatcggg   6780
tagtttcggg ttgggggaga acgaaccgat cagcttcact ttcgggctac ccggtttctt   6840
gcagagttcg aggatttgat tcgggtagat ggacgcatgc gtcaggctgt cgccgatgat   6900
cagcagcgag agcggtttgt cggacccact gtcggcacga atcaccttca gcgtggagag   6960
accgcgcgcg atcaactcat tctgctcgtt gcgaacatcc aatcggaagg gaacgctgcc   7020
aacttcttcc gctgccggcg tgtatgtcca acgttcgttc tgctggctgc cgcgggcgca   7080
atcgacgtcg taggcatagt tctgcgggtt gatggccaac aacacgttgt cgaaatacaa   7140
gttcatttcc tggccaacga cggcataaat taccggcggt aatcgcaagc ggagagcgcc   7200
cggtagattc tcgttcggtg ctgctttggg tttcgcagcc tcctctccca aaacggcctt   7260
ggaatgcagt gaccatgtcc acaggctcag gcaaatgcac atcagaattt gaaagaccg    7320
catacaagtc ctttcgcttc caagactcgg attaatcttc tggtcacggt agaaacccgg   7380
ttttcaggaa aaaaaatcgg gtttctgagt agtccttact gcaacaggta tataggtttc   7440
cgcaaagaac gacaactcct ccgatctggt cttggaacga atcgcttcga ctcgataaga   7500
tacgccccg aaatccgctg actgaaatca ggagaaagtt cgcccgtcag atcttccgtg    7560
ccgaaacaag gaggttcgca tgcgtcgttg tttaccgttt ttcaagattg tttgcttgtt   7620
gtgcagcgtc gcgttgtgca tccgagtcat ggcggcagac aagactcagg agaaggccgt   7680
taccgagctt gaacaactcg gggggacagt cgatgttgat accgatgacg aagacgagcc   7740
gattatcgaa gtcgatctgg ctgaatcgaa ggtcaccgac aaggacctgt cccgtatggc   7800
gaaatggatc actctcaaga tactgacact ctccaagacc gaaatcactg acgccggctt   7860
gaagcacctc agaggactga ccaacttgca ggaactaacg ctggccaata cccaggtttc   7920
cgatcagggc atgattgttg tgtcaggttt gttagccctc aagctgctgg atctcaacaa   7980
cacgcagatt accgacacag gcttgtcgca gcttaagaag ctggtcgaac tgcaaacgct   8040
ggcactttcg agaacgcaaa tcagcgactc cggtctgcgg aacctgaaag gcttgacgaa   8100
gttgcagaac ttgtacctca cgggaaatga ggtcagtgat ctgggtcttt cgcaattgaa   8160
agggctcacc agtttgcgga cgttgagctt gaatgacacg cgcattacag atgccggcct   8220
gccgcatctt tacaagctga cgcacttgca acggttgaac ctcaccggtg cgcaagtgac   8280
cgatgaaggg gtcgaagaac tgcagaagaa gctgccgaaa ttgaaggtgg cacggtaaca   8340
ggcgaaaagt tcaatgcctg tgctagaaac cttgttttca ggaaaaaccg ggtttcgttt   8400
aacgcgagaa ctcgcgttga agctgcgcga ccatggtgtg ctccaggtgt tcgtcgcggc   8460
ccagtacaag ccagcctgac ggtgtcgatt ggccgacgac caggttcaaa tcgcgctgca   8520
ggggattgct gttttggaac gtcgcaccgc cgggtgtatt ggcggcaatc cccggcaggt   8580
cttcgcgttc cttgaagact tcgacaccca ccaagtagcc gccggctgtt ggcgtaatgt   8640
tcacgaaagc tcgccgccga atcgattgca acgtgctttc caaacggttt tcgagtcctt   8700
gtgagtcgcg gtgccaggt tcgaggatat tggaccctac cttgggtctg gtctcaatga   8760
ctccgtccag tttgttctcg cgggcgattt cgaaatagtc gtggacaaca ttcacagtcc   8820
gttcccagac cgcctcatcg tttgtcgcgg ggacaaagaa cgggttggcg gcggcaaccg   8880
```

```
gcgggcgcat cgtcatgcat cccccgccaa cggcggggca gcacaaaatc agcagcagca    8940
ataggttacg tggcatgaac gattgtcgtt tgggagagaa ccgggaagta tctgacgttt    9000
tttgcagcga gaattgaggg agtctgaaat ggggcggtag tttgccatgt ccactcaatc    9060
cccacaagac cattttcccc cggaatttgt cgagaaaaac aggccattcc ctctcaaaac    9120
ggtgtgcatc ttccgcaatt catgcggcac cggctccctg agtttgtggg ttgattgtcg    9180
gttcctggcg cgtcttccag agctgagtca cgttgcgttc gatcattgcg agatgtcgt    9240 tcaaaggcag gtggctgagg ttggtgactg caaatgggtt ctgcagttcg atgccaatct    9300
ggtccagcga gatcaacgga tatgcaacca gcatcgtaat gaacggaacc agccagtcgc    9360
tgtcgatctg atgcagcaac gcaaacggaa gtgtcagaag aaataacgcg atgaaccgcc    9420
gaatcttgat ggcgtacacc aaaggcaatg gagctttcag aatgcgttca cacgctccga    9480
tatgatcgat caactcggct cgctcgcggt cgagttgtag gaatgcaaat cgatccatgt    9540
cgaaacggtc gcatgcttcg tgcaacagat cggccagctt catcgccacg aaggtcggtg    9600
catgctcagc ccgccccacc tggttggcgc gttccacacc gatcagttcg gcaacctccg    9660
gtgcaggggg ttctccgcgc aatgtgcact tggccgcgta gggaaaggcg gcagtccatt    9720
tgatcatctg ttcgcgccaa tcccggtcgg cagggccata agacagtgcg tcgatagcca    9780
ggttgcgaga ttgattgacg atgccgcccc acaactttcg cgcttcccac cagcggtcgt    9840
agccggaatt agtgcgcagg acgagcaaca agcccagcgc cgcaccgacg atctcgaaag    9900
gggccacttc caggccgatg cgtatgtgaa agtgtttctc tgccagccac gccagcaaac    9960
aaatgccggt ggcaatcagt ccgaagctga gaatataggg gagcgcgtgc agcgtgaccg    10020
agccgcgaat cgcacatgcc tcctgccaga aaccttgtcg aacttgagta ttcataggat    10080
ttagctcctc gatcggtgat tgaatggttg aaaggattac ccgcgagaag ggctggaaga    10140
gatcagcggc gctccctcca tttgcccgag tggttggaag cacttctctt cgtccgagta    10200
cgcgaaaacg tcccccgatt cgattttgta gacccaggcg tgcaggttca gtgctccgcg    10260
agcaatcttg gcccgcaccg cagggtgcgt ttccaaattc tcgatctgaa cgagcacatt    10320
ctcctgaatg gccacgttca gcaattctgc cggttccagg tggccgtaat tctcatgtac    10380
gattcgccgt gtcgtctcgg cctgagacaa ccattgggca acgagtggca tcctcttcag    10440
cgattcggga tgcagcagac cttgcatcgc tccgcacaac gaatgtccgc acacgatgat    10500
atcgctgacg ccgagcgcat cgacggcgta ctcgacagtg gcaccttctc gccgttgga    10560 agcaccataa gccggcacga tgttacccgc gttacgcagc acaaacagct cgccaggctc    10620
tgtctgcgtg aacagattgg gaacgattcg cgaatcggaa caggtaatga acaatgtcga    10680
cggggcctga cctttcgcaa gccgttcgta cagctcgcgt tgttcgctga caaatggtt    10740 ttgaaatcgg tgaataccgg ctacgagatg acgcatcatc ataatctcct taaacaggtc    10800
gcttcgaaaa tggcgtgctc cgcaggttcc gatatggcca tcgaacgacc aaaagtggca    10860
cagcgtgagc atcgctctga attttgaatg agtgatggac gagactcgat gagcgcgcgg    10920
caaggctgga gcaggcatca atgtgctgcg actgctgaac tgatcgcaga acgaagcgga    10980
tgacggagca tcaagttcga cgtcggttca gacagcagac gggcgctcga atcggtggtc    11040
gatccaaggc ctgcggcaca cgaactggca gggcagctgc gcgcgagcgt ccatcaacag    11100
agcaacgcgg gccctgtggc attccagctg aaatgttcgc tcataccgcc gtggcgaaca    11160
ggcgcgacac gaagctgcct gccgtggcat tccagtactt ctgcgcgatg tgcgaagaag    11220
```

```
cgaatcactt tgggtcggct gatgcggccg acatgccgga tggtggcatc attcaattcg   11280
atgtcttcgc cgggtgaacc atcttcgaca ggatcggtat ccggcaccga gtcggattca   11340
tcccccgccc aataagccac tgtgacgaga cctctgggaa tggtcgtggg aacgaccatc   11400
aaccccatcg cgagcaacag gcacatgacg ggatagtcgg ccagcgcaat tctgccgaga   11460
aaaccacccg aaatgagacg gaatcgcgat ttcatcagag gacttgatcc acttcgaaga   11520
aaattgcagg aatctactta agcatcggaa ttttaacggt agagaatgac agcttcaagg   11580
aaaattcgcg gatggggatg aattagtcga gccagatgcg ccagcacctg gagtcgttcc   11640
acatcacgag acgtttgaag ccctccagac gctgacgctt tctggctcgc ctgaattgcc   11700
atgcagattc tcaagtgtgt aatgtatgag ccataagaag taagcattga ctgccgtcca   11760
ttactcctgt ttgccgaaag actttcgcat gtcgctcgcg cggaaacatt gcatcgttct   11820
gcttttggga attacatggt gcctgggaat atcggttgcc gatctgttcg cgcaggcgtt   11880
cagtacgttc gatgcggcca aaggggcaca ggtgtttcga cagaagtccc cggtccccgg   11940
gaccgccgat ggcaatattg tctgtgaagc ggaagagttt cagattgaaa agccgggcgg   12000
ctggcaggcg ggcaattggg ggtcgaatta ttatgcggcc acgtttgcca attcgtttct   12060
gagccgaaaa gcgtatttga gtgcacccgc tcaatgcgag cggtcagtgg cgacgattga   12120
agtcaatgtc cccgaggcag ggcggtatct ggcacttgtg cgctacgagg ccgcctatcg   12180
cttcgaaacg cagttccatc tgcaaatcga gcagggggt aaaaaacagc tcgaccgtct   12240
gtatggcgcc cggcagaatc tcaagatctg ggctttcagc cagaagttga accggaact   12300 cgcctgggat tgggggccg tcgaaaatgt cgtctgggaa gggcacgatg cctacgtcga   12360
gctgcagccg ggtatcgcga aactgacgct cgtggccgac aagcaggtgg ggaactcggc   12420
caaacgcaac gtcgacctcg tactgctgac gaagaatgac gccgaggtca acagcgcgt   12480 cgataaggag aactatctgc ctctggacgg catgttgacg cagggcgagg acgtctacct   12540
gaaagtgcat aatcaggcgg atggctcgcc gatgaagctg actatccccc catgcaccga   12600
acattcgccg tactgggtgc acctgagaaa atggaaagcg aagagcatcg ccgtcgaagc   12660
ggggaagtcg accgagtggg aggaagtggg ctcattgatg gatagcctga acgacgggca   12720
atggaacttg gccgcagccc cgacgatcaa agggcagcg ttgcattaca aactcgaatt   12780
cggcgtgaag gatgcgaagg gggcgattgc ccgatcgcc atgtttgaaa gccgggccgg   12840
tacgatcggc atcgccttcg atgccgacac gcgctactcc cgccgcatac gcacgacgga   12900
cggcgtcctg tatgacctgc tcgattatct caagaagaac cccgtaccag gcaagcttcc   12960
ggaacggacg ctcatctacg ccaccacgtt cgacaaacgg cccgacgatc ctaaatataa   13020
cgcggccgtc gacgaattct cgaagatgtt tgcgctgtct gtccgcgatc cgaaactggt   13080
gcagaacaag gcatttcctt ccgggtacgt cgacgtgcgc ggcaatccgc tcgacgaaaa   13140
aatgtacaag gcctggcagg ctgacggaac ggccgacaaa atcgccgtcg tcagcctggg   13200
tgacgaaatt ggcctggcgt cgcccccgc gagcgatcag gcaggatttc atcagtggtt   13260
gcaaagcaaa gggctgaagc ctgcggacgt cgtgccctct gcgggagccg actgggcgaa   13320
gatcgtctac aacatcgcgc ccgccatcat gcagaccgag ccggggctgt actactattc   13380
gcgtctctat tcccatcact tcgcgattca gaatcagaag aaaactaccg acttcgttaa   13440
gaagtttctc cccaacgccc acgttggtgc gaacttctca ccgcatcacg gttatcacta   13500
cctcggcgaa acgcacatgt gggcgacgct gtttcgcgaa ggaggcatga cgcttccgtg   13560
gagcgaagat tacatctggc aagttcccat cggcacgcag cagatgaact tcatcagcct   13620
```

```
cgatttgttc cgtgccggat tgaagggaaa acccaacgcg aaaatccagt tttacgtgat    13680
gccgcattgg ggcaatacgc cccatagctg gcgcaggcag ttctacggcg atctggcgca    13740
tggcatgcag atcgtcgact tgtttgagtt ccgtcccgtg caggcggctt acaccgagaa    13800
ccatgccgat cagcccgaga tgtatctgga aatacgccgc tcgttttcgg agctgggttt    13860
gttcgaagat atcgtgcagg atgggcacgt ccgccccgga acggcagcct tgtggttcag    13920
cgagacggga gatatctgga acgacaatcg gcctcccttc ggcgctgcga aacgctgctt    13980
gtacatcgct gtcaagcagc agcaggttcc actggatttt gtgattgaag aggacgcgct    14040
cgatggttcg ctcaagcaat acaggattct gtatctggcc gatcagcacg tcagccgggc    14100
ggcctcgaaa gcgattgccg cctgggtgca gcaaggcggg ttattgttcg cgacggcagg    14160
cgctggcatg ctggatgaat tgaatcagcc gaaccagatc atgcgcgaac tcttcggcgt    14220
cgatcagacg gcgctggata ttgcggaagg ggacacgttg aagcttgaga agcaggatct    14280
ccccttcgcc aaagagatcg acgtcatcac cggaccgttt gctccgggag ccaaagcggt    14340
ccagatgcag gtgattgccg tccgcagccg ggtgaaactc accggtgcga agcaagcagg    14400
cacgtttgcc gatggctcgc cggccgttac attttatcaa aaagcaggct ccaaggggga    14460
cgcctattac gcgggatttc tgccgggatt aacgtacttc aaatccgcga ttccgttgcg    14520
tccggtcgat cgtggttcga ccgacgattc gatgcccac ttcattccga cggcattcga    14580
ccccggcgtg ttgggcgtgt tgtcagcccc catcgacgaa acatgtcagc cggtgatttg    14640
cagtcagccg ctggtcgaga cgagcattat cgaagcgaaa caggcgactc tcattccgct    14700
catcaattgg agcgaaggcc cggtgaaggg gctgacggtg accgtcactg caaaacttgc    14760
aggcaaagcg gccacgctcg ccagcggcaa aaaagtgcag atgaaaaccg agggccacaa    14820
aacggtattc acattcgacc tggatgtggc cgacgcgtta attgtgcggt gacgcctagc    14880
tgtgggcttc aacccacgtt tattcgcgat aatgtgtcgt aagacgattt caagtgctac    14940
aattcgtggc gaaagtgaaa tctttctctg caaagtcacg cttaaggaag tctgtcagga    15000
gttctttatg aaccgacttg tgctgccata tttgcggggc caaattttct ccgcggcgat    15060
tgccttcgtc gtctgcagtg aatggtgca gggcgagaat gaaaaggatg cggcgcagac    15120
agatctggat cgtcgtatcg cgctgatgca gtctgccctc gacgaatttg tggtgacttc    15180
agacgaaatt aaagacaggt cggcactcaa ggtggtcagg aaacccctct gggtctacga    15240
cgatgaaagc cgcaatgttc ttgagtcggg cgtctggcgg gtgggagaga aaggtcgtcc    15300
gactgcatac atcacgctcg aactctatcc tggcggtccc aaaagaggtt tgctgaccta    15360
cgagttcatc tcgttgaccg attccaattt tacgatgcag tcgaattttg gaatcagatg    15420
gagccccatc tggacggatc tcgaaatgga ggccatcgcc aatgcaccgc agccggcaaa    15480
gacagaaaag gagcggctgg cacaaatgca aaaattatcc gcccgcttta cggccgtcca    15540
aagctatcgg gggaaggaaa tcgatctgcg ggtctcagac gatccgatcg atcgttacag    15600
cgatcccgca aaacagattg tggatggtgc ttttttttgcg ttcgccaacg gccttaaccc    15660
cgaattgggg atgatgattg agaccgacgg aaaaggctgg acgtatggta tctttcggat    15720
gggaaccgca ggtgttgcca tgaagctgga tggcaagaag gtacagggcc tgcatcccaa    15780
cacgtcctac ggtgaacttc gctcctacac cgcaacgcgg catggcgtcc agttgatcga    15840
ttgaccaacc tactctttcg ggcggccgat tgctctgatc tctgcgggag acagtacacg    15900
atcgtaaatc cgcagatcgt ccatcacgcc gcgaaagaac acggcggccc cctcatcttt    15960
```

```
tcccacgacg gatgtgcccc ctgttgccgc cttttcttgc gttgtccgcc gggcttcagt   16020
tgttttgccg ttgacgaaca gcctgagcag cttgccgtca aacgtggctg cgacgtgatt   16080
ccattcgtcc atattcaggt acgagttaat accattcgcg ccattggcca cgtaaaagtg   16140
agtcgtctta tctctgtgga aggtcaaccc atatgtcttg ggtcctctgc ccagcagaat   16200
cggttcgccg gcgggcgcag ccagcggttt aacccagagc atcagcgtga atgcatcttc   16260
cacgtccagt tgcgggggca ttccgaagtc gatggcattg tcggtaccgt taaattccag   16320
accttttccg tatcggccct gaacccagtt aggctggcca agaattttc  catgcaatcc   16380 gtgaggtccg ctgtcgcgtg cttccgtgcc ggttccctcg tccagcttcc agtgagcgag   16440
cagccccggc tcggcagccg ccacaggcac agccagaaaa caaccaagta acacagcgat   16500
ggacagtttc agtgtctggg acatttcaac gctcgcagga gatatggttt tcgatctgga   16560
ggaatcgtat ccggtttgat cttaccagtc caatggtata cccgatcgat tgttcagaac   16620
ctgtgagggg ttgatatact gacacgcgtc aaaggtgaaa gcgcctctcg cacgttctgg   16680
agaaaagaga tatgccgagt gatccaggca ggttctgccg gctggcagcc accgcattca   16740
ttgtaacggc tgtctgcctg tgccatcagc cggtcttgtg cgccggcgat acagatggca   16800
agcctgcaca aaggcggaa  aagaaagagg cggccccgca ggtggtcaac gaatacagta   16860
ctcgattatt cattgccaat cccgacggct cgaacccgaa gccgttgatg aatcaatcaa   16920
acttcaaggc acagggttcg ccgaactggt cgcgcgacgg caagttgatc gcgtttgacg   16980
gcgagatcga aagccaggg  gcacagcccc gaaaggagat cgccgtcgtc aacgcggacg   17040
gttcgaacct gcgcgtcctg atcgccggtt acatgccgaa attctcgccg gctgccaatc   17100
ggatcgtctt tacgcgtgcg gctccgcgcg gcatctggat catgagcgcc aatggaccgg   17160
atgaggaatt agtccagatc gatgagaagg gttgggggggc ggattggacg gcggacggcc   17220
gcattgtgta cgtcacccgc gaacggaccc gggcaaacct aatcctcttc gacatcgttg   17280
aaggccgcag cgacaaaatt cttgacgaca acaaatcgac ttattcacag atcttctgga   17340
acctgacttg ttccccccgat ggaaagcgga ttgtgtttaa gggaattcgg aggaacgggc   17400
agccggatgt ggcgatcgtc gatgtccgcg gcgaacaatt cggtatcgta cagcgcgttg   17460
cgggaaacgt ctggcccggt ttttgcgtgg agtcccgacg gaacgcgaat tctgttcagc   17520
tccatgaacg acacacaaaa gcaagaccag ctctcgttca tcgatcccaa taccgacgca   17580
gcaccgcaac ttcttcccgg acaagacgcg cgccgacgcc ataccgatct ggcattttca   17640
ccggacggaa aaaagatcgt gatctcgatg ggaatgccgc cggcgcccgt tggcaaatag   17700
aagtgatcgc gaggttgatt ttgcggtgat ggtacaacat cgtaccgcta cggagagaac   17760
tctttgcgat gaactctcac atccggcgaa gcggtgattc cgattcgagc acgttctttc   17820
gagtcgatgc aaataaaaac catggttaca tcgccgtaaa tcggcactgt gatattcttt   17880
ggcagcttaa ttcgcctgaa tcccttggcc gataaatcca gaatgagcgc tatgacgctt   17940
tcttgagaaa tatcggtcac gcgcacctcg attgtgtcgt cgaagaggat cgattgattc   18000
agggcgcgcg ataacaccag cactgaaagt ccctcgccaa ttcgcggttc ggcaggagcc   18060
tcaccctccc gacgacgatt attgttcgtt ggtcgcgggg attgcgttct cgttataaag   18120
cggcaagtgc cggtagtaga cttccagcat cagaatgcac atcgacgtaa tatacagccg   18180
gcctccctcg gcggtgtgtt ctttcggggc accactcact ttgaacgggt ccagctgcc    18240 ggcctgtttg ccgagtttca actgactctt cactagttcg tcacggagcg ctccgttcca   18300
tttctcccag gcttccccct ggatattgtg cagggcttgc gtggcgtagt accagaagta   18360
```

```
cacattacgg cggccgttcg accagtttgg taaattctcg tcctgcacca ggtacttgat   18420
gccgtcgcgc atggctggat gtttgggcgt ccaaccgaga tattggcggc acagcaatcc   18480
ttccgccgtc atggccggtg aaacggccga tggcgggttg atcggctcgt atttgtagcg   18540
tgcgccgttc tgctcctgca ccgagtcgag aaatacgatg gaccggtcca gcacctcttg   18600
agggacaggt aacccagcca tccgtgcact ttggatcgcc atcaattgcc agccgaagac   18660
cgacaagtcg ccggcactgt tcgggcgata cttccagccg ccggccgtcg ggtgctgcga   18720
tgtgtagatg aattcgagcg cttttttgcac gtggggcaac agctcgctgt cgtgcgtaat   18780
cgcataagct tcgcagagca cgatcgtcgc ctgcccgtga gcgtagaacg aagtctgccg   18840
gccatcttcc agcgcatcgt gcaggtcgcc gttcggtttc tgcactttga ccagccaatt   18900
gatccctttg cgcacctggt ttttgtacgg cccttgctga ggcgtgtgcc ctgctccgag   18960
aaaggccagg agtgcgagcg aggtcgctcc cgtgtcggtg cggaggctgg gcattcccgg   19020
gtcggggtaa ccttggtgca gctcccagtg accgtcaccc ttttgttgtt tggagagcca   19080
gttcaacccg aggctgaccg tttgctcgga tctttcagaa ccgccgtacg atttgacgag   19140
cccaccgcgg gcacccgtcc cgcgtccgct gagtgccgtg ccgactccta cttccgacgg   19200
gttcacgctg acgacttccg acggcccact cttcgcccct tcggaatcgt ttttttcatt   19260
ttgggtttcg atgacgcccc agcttcttcg ggatcatcgg gtttgccatc cggctcgatc   19320
tttatcgatt gaatttcgac ggcagtccgt ggggcttttca ccggtccgat gtattcgccg   19380
agccagcctc cgacgagcgt cgggatcctc ttctgttttg gataatgaat gacgatcaat   19440
gcgaggatca gcaacaccag gacgtgcact cccaggctga tgagccagct tcgtcccgat   19500
tctttcgcct catccttcaa gacctcgagg atcggttttt cttcgacgat aatcggcgta   19560
tgtgcgacct gaaacgggga cgctggggct tgagccgccc gacgtcgtac cggtcgtcga   19620
cccgaccctg tgggtcgga cggcggtgtt ggcggttgcg ttttagccat gcacgaatca   19680
cttgagaatg acggcgcgag aagaactcag gaaagacgta tctttcagtg tacgcaaact   19740
ggcggccaag atgaagctga gacgatgaga tggggagaaa ttgaagatcg aggattgaag   19800
atggaagatc gtaaaaaaag agtggtgcga cggcgtgtta cagttgccac aggcgtgcct   19860
cttcgcgtct ttttttccaat cgaaactcgg gaatcgaaat tcatcccgca ctgttgcgga   19920
gcaatatctc gcctccagtc attcctcgcc ggcctccgcg ataagcagcc cccgccaggt   19980
ggccggtatt cccgttgacg cggatgcggt cccctttcat ctcggcaccg aaccaatcgc   20040
ccgtgctgcc gttcacgacg atttcaccgt cggtcatctc ggccccgacg tgcatgccgg   20100
catcgccatt gaccgtcatc tttccggacg tcatcagcgt gccgatcaat ttgacctgcg   20160
cacaggtccc ttcccagacg atttcgctgt cctcattggc ctagccgctc acatcgaaga   20220
attcaccgag cgtcaggcgt tgttgccgt actgcaccgg ggtgccgcga acttcgtcga   20280
tcaattgagt acgaacggtc tcaacacgga tggcgtcaac ttcgatgaga attgaggttg   20340
cgttttcagt gtcagaacga gaggcatatc gcggttgagg gtcgaaggct aaaggtggag   20400
gaatgaggat agacgattgc aaggggaggg gtaagttgcc atggtcttag cgaccaatcc   20460
aaaatctaaa attccctgcc tcattttccc acgacttttg ccgactgcgt ttgaaattca   20520
cgttcgagtt cgtcggctgc taaagctcgg ttgtaaatgc ggaattcgtc gagttgaccg   20580
gagtaccatt gcgaatgagt ggcgacgtag caacccagtt cgaggggta agaggcggtc   20640 gccccgattt tgccgtcggt tcgttctttg ctgccggcca attttccatc cacataaatc   20700
```

```
tgcagcactt tcttttccgc gtcgaagacg agagccacgc acgaccattt gtcgacggtc    20760
aacggtttct gcgacgcgag cgtatcccac tctttgtcgg cccccgaacg cgtctcaaaa    20820
cggggcagcc cgtcgggacc gatgtacaga ttccaaccct gtttggaaat aacgtaaccg    20880
ttgccagcca gcttgtcggg gcgaatccag atcgagaccg tcagcggccc gctcccctgc    20940
aggatcttgc cgttaccgca gttggcgaag ctgtctttgc cgttgaacgc gagcgccttt    21000
ctgccgactt ctccgacgag ttgggcattc gtcagctgca tcgaattacg gctgctctgg    21060
cggtcgcgga caatctgccc gctgtcgtca tcgaagtcgt aatgcgcaat caggtcaccc    21120
tgtggctcca cagttttagc acgtttcggt ggggttttg caatggtgat gtctgcggga    21180
atcggcaacg agtagatgtc gaacccgccg tcgcgcatgg agatgaatgc aatcgattgt    21240
ccgtcgggcg cccaggcggc atggtcgtcg aaggcagagt gctcggtgag attccgcaat    21300
cctgtcccgt cggcccgcat cagaaacagg tcttcgttgc cggtccgatt cgacgtgaag    21360
gccagccact ctccgtcggg ggaccacttc ggccggcaat cgacgcctgg ggcttcggtg    21420
agccgcgtga gctctgtacc atcggcacga atcttgtaaa tttccgggtt gccgtcgcga    21480
tcgctggaga aggcaatcca ttcgccgtct ggcgaccagg cgggatgaaa gcaatagttg    21540
cccgcagtct gcacgagctt ccgttttcct ttggcgtcgg catcgaaaat ccaaaggacg    21600
tggccgaccg tggtggcgac gatctctttt ccatcgggcg accagcttgc ctgctcgccg    21660
acattcacgc cgtcaccggg aatcagcttc cgcagatgcg aagctctgaa gtcttcgccg    21720
atgtcacaga tgaaggcatc ttttgccgag ttgcccgtat cgttgccacc gcccgtgacg    21780
agcagcgact tgcggtcggg agaccaggag ccgtattcct gaatctggac cgagttttcg    21840
aactcgggca acaaagcgcg gtccctgtg ccgtcggact tcacgatccg catccccatg    21900
agcaccttgt tatcctgccg gcggttggct tcgtaatgct tcgaatacga caaatgcgaa    21960
ccgtcgggcg tgtagctcag gaaaaacttc gtgaagtaac tccgtgtgat gcgctttacc    22020
ggaggagccg tgctgttgtc ggaccgggcg tcggtcacga agaggccagc gagcacggcg    22080
agggttaata gtgtttgaaa gcgggacatc gcgcttgtac cttgtcaggt cggggtgaac    22140
cgaggatagc agctcgagga tagccaaaaa tgcactgatc gactttgagt atttccgcta    22200
tcttcgatcc tctatcttcc atttctcaac cataccgctt atcccaactc ggcgattggc    22260
ccttcgagca cgcttgcatc gcggtcgccc aaggcgaggc ggtcgaggcc cattttgtgg    22320
aagacagtcg agatcaggtt ggcggggtgg acggggtgtg agcggggta accaccgtcg    22380 gcactcgatg agccgagcac cagtccaccc ggaacgccgc cacctgcgac gaaggcggag    22440
tagacccagg gccagtgttc gcggccagcg gccccgctga tctgcggact acggccgaat    22500
tcgcccatgg cgatgacgag cgttgtctcc agcaggccgc gatcctgcat gtcgtcgagc    22560
aaggcgctca gtgcccgatc gtaaatcggg cagtatcgtt cctgcatccg ttcgaacagt    22620
cgatagtgca aatcccaacc gccgtcgccc ccttgctgct cgtcttcggc atcaccactc    22680
cagttcacct gaacgaaagg gacacccgct tcaaccaatc ggcgtccgat aatcaggttc    22740
tggccgtaga tcgtccgtcc atatcgatct ctcagggctt ctgattctgc atcgaggttc    22800
aacgcccctt tggaagtcgc agatgtgacg agagcaaatg ctttttgcct gaggtcgtca    22860
taccggccga cttcacccga ggcttctagt tgttttggga gcgtatcgat ttcggttaag    22920
agggatcggc gagttcccag tcgatcggtg ctgatttcgc gcaacggttc cagcgagcgg    22980
gggacgcgga ctccttcctc gaaggaaaag ccttccagcc gaaatggatc gtgaggagcg    23040
ccgagcaccc cggccatttg accgcgcaga ttctcgccgc tcactttaca gatcggtcca    23100
```

```
atgcatgtga acgcgggcca ggcggaggag tggccgcgat gcatgtaaga gatcagcgat   23160
cctatgctgg ggcggaccgt gccggggaac gggattccgc cggaagcctt tgcaccgaac   23220
acgtggccgg tgagcccgat cgtgccgccg acgttgtggt cttttgatc gtggttcata    23280 ctgcggatga tggcgtactt gtcggtacgc cgcgccaatt gcggcagcag ttcggaaatt   23340
tgggttcccg gcgtggccgt tgcaatcggg ttgtagcaac cgcgaatttg agagggagca   23400
tcgggcttcg ggtccacat ttcgtggtga cttggaccac cccacagcca gaggagcaac     23460
accgacttca ccttcgacgg cttcgcgaca tcggcttgag cctggccggc aagccattga   23520
ggtagcgaca accccagcgc cgagcacgtt cccacctgca gtaactcgcg gcgcgtcagt   23580
ccctgacagt cgcgggttcg caatcgaccg agattgaaca ttccgagatt ccttgtttat   23640
tcggtggcga tcgattcacg aattcgacaa tgcttgacgg aacccgtaga acgggacga    23700 cgcctagtgt ttatgatacc gcctgtgaga cgcttcgcca agaaaaacg gaaccctgtc    23760 tggtatcggc atttgtggca cggtaccccg aactctatcg caaagatcg aaggcgttcc    23820 tgtgatcacc aggactatcg ttgcccttcc aatgtcagat cgacgacttt cgtcttatcc   23880
tttgcctcga ttgtcgcagt caggccggat gtttcgccgg tgtaatattt ctgcggtaaa   23940
attggcttgc cgggtttctt ggcgacgggg tcttcacctt caaatacgtt gacgctgatc   24000
ttgtagctgc ccggtacgac gccgtctttc ttttcaaaag ttgaggcgac gtaatttccc   24060
ttggaatcga tttcacccgt agccaaatgg cccttgtcgc gatcgacggg agaaaacagg   24120
acacttcccg tcgtcacagg ttggccattc cacacgacct taccactgac cggtatgggt   24180
tttggctttc ctggagttcc accaccgcat ccgctgaaag cgagacagag cacactgctg   24240
cagagacttg cccacaagag tagccgcatc gattaacact cctgcatcga tccaacggga   24300
tgaggacttt gtccagaact aaaagtcacc gacgacttcg ttgcccgact tggtgccgag   24360
tgcacccaac gtggccaggc tgacattctc gctgatgaac cggaccgagc cgtccacgag   24420
cagaaaatga gctcccccga cgtggtagct cgcaaaacga tggctgttct ggtagtagcc   24480
ttccgttaca gttttgttgt tgatgccggt ggctgtggac gtctcctgga agcaggcgcc   24540
ggtccatgct ccatattggt ttccaatggt accgttgtaa atttgtttt cgccgatata    24600 cagagtattc gatgttccat ctgtgacatc gcgaatgctg atgcggtccg gaaaattgtg   24660
catcattcca cgagacaagc ctggcgtgct gtccacaacg taactgctga aaaagcatgg   24720
gcaggcgacg ttatcgcacg gcacgtaggc tgtgccacac gtgtatcctg cctgaggacc   24780
gccgctgccg atgtaattcg aaacggccgc ggttgtcggg gccacgttgt ctccgtcatt   24840
tgtcagattg gtgagcactc gctgtccagg gtcgctgggg caggaatatg ccggaatgac   24900
cgtcgtgtgc acagacaagg cgaacaggta tgttccctgt ccgctggctg ctactccacc   24960
agctccgcct ggaatctgca tgccgaacgc cggcccgtac gtcgcattgc tcgccgaggc   25020
caattggtta tacagcggtg ctccatcaat gtaaggcagg atccagatac gccagttgaa   25080
cggcatgcgc ggcgccgcac cgctgccgta actcgtaccc ggactattgc cataagggaa   25140
gacccggaac gtatcgtggt aattgtgcag cgccaatccg atctgcttga gattatttt    25200 gcattgagtt cggcgggcgg cctcgcgtgc ctgttgaacc gccggaagca ataatgcgat   25260
taatacggca ataatcgcaa tgacgacgag caactcgatg agtgtaaatc ccaaccgcct   25320
ccgccggaga agaaacatga tcgcatccct tttagagagg tctcgagaag taaaaagaac   25380
aataaagctc aaccgaaagc agatcaaccc gcgatatttc aaaaacagat gtctgatgtt   25440
```

```
ttaagttcaa tggcgggaag gcgctgtccc tttggatagg acaaatcaat tggcattgat   25500
ggttagtttg cagcgttcga aatcgtatgt caagaagaat cggggttgcg tagcacgttc   25560
ctgattacag cttcaacatc tcccgcagcg cttcgagcgg cagtccgacg acattgctga   25620
tgctcccttt cacgctggca atgaacaggc tgcctgctcc ctgaatcgcg tagcccccg    25680 ccttgccgcg cggttcgccc gtagaaatgt accagtcgag caacggttcg acgtcgtcga   25740
taaatgtcac ttcggtgtgc acgagccgtt cgagacattt gccggccagc gtctgcacgc   25800
agatcgcgga gacggcctga tgcgtgcgac cggcgtaata atttcggaac caatgtcgca   25860
cgacgtcgga ccaggtagcg tcgtccggcg gttgttccaa tgccagcggg gcgtgagcat   25920
cggtcacaac gatggtcgta tcgcctgtga cgatgaacgt ggtttcacct gcgagttcag   25980
gcttactggt ggcgatttgc tccaggacgt cgcggccttt cgaccgcgca atttccatca   26040
atgtcacctc gatggaggcc accgttcgca gttccgcaag gctcgcttcg ttggcatcgc   26100
gcggcggaag tacttcgatg gatgtgttcg gcactaacaa actcaacaac tcccgcttcc   26160
gcggcgaccg cgaacccagg atcaccttga tgtctgataa cgattgcatg aatgtaaaaa   26220 tcaaagttc ttagccgcca ctttataagt ggcgatcaat tcgctttgca aacgtggagg    26280
tcacacaatt gagttcgacg ccacttgaaa gtggcagcta tatggaattt acctgttcgg   26340
aggtcgtagc gtctgtcgcg tgcccgcctc cgatgtgcac ggttttccag aacaacagca   26400 acaacccaa cgctgccacc gacggaatgg caaataagat ttcgaaattg tgtttgaatt    26460
tttcgaacaa taatccaccc agcaatgcgc ctagcggcat cccgattccc agggtcacga   26520
atgacagcag gttctgggcg ctggctcgca aatcggcccg gcagttggca tcaatgtaca   26580
actgggcgac aatcaccaga aacacatggc agacgccgtg cagagccaac ccgacgatca   26640
ccagccacca cggagtgccg gccgaaaata atccgtagcg gatcgcccag gcggtgatgc   26700
ctaacgcaaa cgtgacgcgc aatcccaacc gtttcagaca gaaggcaagc aacatcaacg   26760
cgggaaattc tgaaacttgc ccgacgagca tcactgtcgg aacccagttc tcgtgcacgc   26820
ccatcgtttc cagcaggacg ggaacggcca ggctgtagag cggtacgacg aggactgcca   26880
gcagaaaact gaccatcata aatagtgaaa agttgaagtc gcgaaacatc gagagaatgg   26940
ccaagggcgc cacccggtcg cgtgctgact tctccggggg tgtgtgtggc agaaagacgc   27000
aaaaactgct taaggcaaac gatagcaacg cactcattcg gaaacagtcg gagcgggagg   27060
gccgcgggag ccagcggagc agtttctgaa tttgagtaat ccacgaccag tccgggtgat   27120
gttgctttaa ccataagaag acctggtctt cgccagcca taacgaaagg gttgcgccgg    27180
ccaacatcca tccgacggtc ccccagacgc gaactttgcc gaattgaccg tctgggtcgg   27240
gcaagtggcg gaagcagagc gaggtcgtga gcggtacggt ggggaaataa gcgacggcga   27300
agattccgca cagcgcgagg agcgaataaa aatttgcccc cgtcgcgccg tgcaactcgg   27360
cagcaaccgc cagcacgtaa agcgaaattc cgccgacaaa gtgactgagg gccaggtact   27420
tttcagtggc catccagcgg tcggccactt gtccgacgac aaaaggagcc agccacaggc   27480
cgatggcggt catcgccatc aattggcccct gctgatgttt cgagagatgg attgactccc   27540
aataaatcgg gagataggtc atgatggtgc cggagatccc ccactccaga aaccacagca   27600
ccgacaatcg ccaccgcaaa ttccagcgca atcgattcga catggtcgaa agcataacgc   27660
aaaggtccga attcgtcttc tgtggttttg tagaatattg atgtgctggg gtcattgatc   27720
ggaagagtgg ggttcccggg tcagccggtg tcatttttgtt ttcgcgaaga aagatcgaaa   27780
ctcgtcaata tggccgttaa cgcaactcct cagtatcaaa aggcggaaga agcctatcgc   27840
```

```
cgcgcgcaaa gcgtgcagga gcaaatcgag tgtctggaaa agatgctcgt ggaactcccc   27900
aagcacaaag catcggaaaa ggtccaagcc gacttaaaga cgcgactcaa agatgcccgt   27960
gctgaactgg tcgcagagaa ggcagcaccg aagaaaggga aagttacaa gtttccgcgg    28020 caaggagccg gtcaggtggt cattctgggt ggcccgaacg gcggaaagag ccgattgctg   28080
gccgagctga cgaacgccac tcccgaagtg gctccctacc cgtttacgac gcgagagccg   28140
cttcccggca tgatggactg ggaagacgtg acggtgcaac tgatcgacac gcccccgatt   28200
accgacagca tgttcgaaag ctatctgccc aacattgtgc gatcgacgga cgccgtctta   28260
ctctgctttg acgaagttc ggacgacgca cccgagcaga cggtcactgt cattaagcag     28320
atggaagaac ggaagacgat gctggcggtc gaatcgggat tcgtcgacga caatttctca   28380
ctgatccgcg tgaagacctt gctcgtcgtc acgcacggag acgacccgg acgcgacgac     28440 cggctggcat tctttcacga gatgttgccg tcccagtcct ttcaaacgca aatggtggaa   28500
tttgatcggc cggattctgt gcaggaactg agaaaccgga ttttcgcgct gctgggtgtg   28560
attcgcgcgt atacgaaagc ccccggcaaa ccggccgact acacttcgcc tttcactgtg   28620
cccatcggat caatggtgga agaccttgcc ggcaaagtac ataaggattt ggcagacaca   28680
gtgaaatacg caaaaatctg gggaacgagc gttgctcacg cgggcaaag tgttggccgc     28740 gaccatatcc tggccgataa ggatttagtg gaattgcaca cgtaaagaaa tccttccggt   28800
cagcctttcc ttgttgctgt tgcatcaaga gttgtttata ctgagtagat tggagaattg   28860
ttctaaattg taagcttcaa tccggtatcc atccgacgcg caagttacga ttgaatgctg   28920
gcttaaggat acatgctcag ccggtggggg taacgagtgc agcctcgtga ttgcataatg   28980
attcagtatc aatgaactgt tttcgtcgtt gaaggaacag gcatgcagcg taacacggac   29040
cagaattcgt tcgccccgtg tcaccctacc atcactcgaa ggttggcact gcaggccggg   29100
tcgatcggct tgcttggttt gggaatgaac cacgtcgagg ccctgcgggc ggccgcgacc   29160
gctgagtctg gcggaaaagc accgccccc aaagcccgtg cggtcatcta catttttctt     29220
tctggtggtt tggcacaaca agacagtttc gacctcaagc ccgatgctcc gcgcggcatt   29280
cgtggcgagt tcgatccgat agcgacgaac actcccggcc tgcaaatctg cgagcacttg   29340
ccgcagttag cgcaacggag ccatttgtgg gctttatgcc gttcgctttc gcattccacg   29400
aataaccatc gcgacggcca cttgatgatg ttgactggac gcggggtgct gtcgccgggg   29460
ttcaacgcct cgatgccgac gccgaccgac tggccgtcga ttgcgtctgt cgccggtgca   29520
gtcacccggc ctcgcaacaa tctgccgccc gccgtcgtat tgcccgataa aatcattcac   29580
tattcgcgac aagtagttcc cggtcaattc gccggcatta tgggtccgcg tcacgatccg   29640
tggttcattg aatcatcccc attcagcccg cgcacttacg gagcgtatcc cgaatacgag   29700
ttcgatcacg aacgacgtcc aaacatgccg ctgcggacga ccttcgaagc cccgaacctc   29760
acccttccgg aaggttttgg gaaaagccgt ctggggagcc gtctcgactt gctcaatcac   29820
atcgacgaac agcggcgcga cttggacaaa ttcgcccata tcgaaaactt cgacaggtat   29880
cgtcagagcg cgatctccct gctgactgac gcccgcatgc ggcatgcgat tgacattcaa   29940
agtgccgcgc ctgaaatact caatcgttac ggcaacaact cgttcggctg gtcgttgctg   30000
atggcgcgac ggctggtcga agccggcgtc aacatcgtgc aggtcaacct gggcaacaat   30060
gaatcctggg acacgcacgg taatgccttt ccgcatctca aagaaaaatt gtttccgccc   30120
accgataagg ctctgtcggc cctgctggat gacttgtccg aatgcggcat gctcgactcg   30180
```

```
acgatgattg tcatggcagg cgagttcggc cgaaccccgc atgtttccgg tgggggaact    30240
gccgtctacc aatacccggg ccgcgaccac tgggggggcag tgcaaacagt gttcttcgcg    30300
ggaggcggag tccgcggcgg gacggtcatt ggctccagcg acaagtatgc aggttatccg    30360
gccaccgcga aacaaacacc agaaaacatg ggagccacga tttaccaggc attgggtctg    30420
cccgacacga ctgcatggtt cgatgaaacg aaacgtccgc accacattta tgagggtgac    30480
ccaattcccg gattggtcta gtcgtgactc ggagtcaatt gatgcggaat aaatccaata    30540
cgccgacgat gtccccaggg catccttgtt tttcacggcg tgtggccttg caggccgggt    30600
cgatcgggtt gctcggtttg gggatgaacc acgtcgaggc tctgcgagca gcggccgctg    30660
ctgaatcggg cggaaaagcc ccggcaccca agcgcgatc ggtcatctac atattccttt    30720
ccggcgggct ctcacagtta gacagtttcg atctcaagcc cgaagtgtcg cgtggcattc    30780
gcggcgagtt cgatccgatt gcgacgaaca cgcccggcat ccagatttgc gaacacctgc    30840
cgcaactggc gcaacgcagt catttgtggg ctttgtgccg ttcgctttcg cattttcaa     30900 atggacatcg tgaaggccat ttgatgatgt tgaccgggcg cgggatgctg tcgccgggct    30960
tcagcgactt caaaccgaac gcgaccgatt ggccgtccat tgcggctgtc gcgggtgcag    31020
tgaccaagcc tcgcaacaac ttgccgccgg ccgtcgtttt gccggataag atcattcaca    31080
attcacggca agtgatcccg ggtcaattcg ggggaatgat gggcccgcgt cacgatccgt    31140
ggttcatcga atcgtcgccg ttcaatccac tgggttacgg ggcctatcct gaatacgagt    31200
tcgaccacac ggagcgtccg aatatgcctc ggcggacgac ctttgaagct ccgaatctca    31260
cacttcccga agggttcggg aagggccgtc tgggcagccg cctcgatttg ctcaagcaca    31320
tcgacgagca acgacgcgac ttggaaaagt cgcccacat cgaagatttc gaccgctacc     31380
ggcaaagcgc gatttcattg ctgaccgatg cccgcatgcg gcaggctatc gacattcaga    31440
gtgcagagcc ggaaatcctg aaccgctatg caacaactc gttcggctgg tcgctgctga    31500
tggcgcgacg gttggtcgaa gcgggcgtca gcatcgtaca ggtcaacctg ggtaataacg    31560
aagcttggga cacgcacggc aatgccttcc cgcacctcaa agacaaactg tttccgccga    31620
cggacaaagc cctgtcggcc ctgctggacg acctgcgcga tagcggcatg ctggagtcga    31680
ccatgattgt gatggcgagc gagttcggtc gcagcccgta cgtttccgga ggaggaaatg    31740
ccgtctacaa atacccggc cgcgaccact ggggagccgt gcagacggta ttttcgccg     31800 gcggcggagt tcgcggcggc actgtcgtcg gttccagcga cgttatggca ggtgctccgg    31860
caaccgccaa gcagacaccc gaaaacatgg cggctaccat ttaccaggcg ttgggcctgc    31920
ccgacacgac tgcatggttc gatgaaacaa aacgtccgca ccacatttat cacggcgaac    31980
cgatccccgg attgacttga tcttcccccc cctttagtaa ggaggggcag aggggtcgcg    32040
cgacagacca tcgactgaca acagaggaaa cagggattta tagactgctc acaaagcatc    32100
cgtcatccct ttcagactgg gaatcaacac atgcggaaca taaacaatac gccaacaatg    32160
cctcccaggc atcctggttt cacccggcgg gccgccttgc aggctggtgc gatcggattg    32220
ttgggattgg gcatgaatca tgtcgaagcc ttgcgagctg ccgctgcggc cgagtcggga    32280
aataaagctc cgaatgggaa agcccgttcg gtcatttaca ttttcctctc gggtggtttg    32340
gctcagcagg acagcttcga catgaagcca gaggcccggg ataatattcg tggcgagttc    32400
aaaccgattg cgacaaatac gcccggtctg cagatctgcg aacatctgcc gcaactggcg    32460
cagcgcagtc acctgtgggc gttgtgccgt tcgctctcgc attcgactaa cggccaccgt    32520
gaaggccatt tgatgatgct gaccggtcgg tcggtgcttt cgcccggctt caatgggtcg    32580
```

-continued

```
atgccgacgc ccaccgattg gccttccatt gccgcagtcg ctggtgccgt cacaccggtg    32640
cgcaataatc ttcctccggc agttgtgttg cccgatcgcc tgattcatta ctcgcggcag    32700
gtgatcccgg gccagttcgc cggcgtcatg gggccgcgtc acgatccgtg gttcatcgaa    32760
tcgtctccat tcagtccgcg tggctatggt gcgtaccccg aatacgaatt cgaccacgaa    32820
gagcgaccga acatgccccg gcggacgacg ttcgaggcgc cgaatctgac gctccccgaa    32880
gacttcggca aggcccgcct ggggactcgt atcgatttac tcaaacacat cgacgaacag    32940
cgccgcgatt tggacaagtt cgcgaagatc gaaaacttcg accgctatcg gcaaagcgcg    33000
atctcgctgc tcaccgattc ccgtatgcgg caggctatcg acgtggcgaa tgccgccccc    33060
gaggttttgc agcgctacgg caataattcg ttcggctggt cgctgttgat ggctcgccgt    33120
ctggtgagga gcggagttaa cctcgtgcag gtgaacctcg gaataatga aacctgggat     33180 acgcacggcg aagcgtttcc gcacctcaaa gacaatctgt tcccccgac cgacaaggcc    33240 ttatcggcgt tgctcgacga cttatccgaa agcggcttgt tggattcgac gctgatcgtg    33300
atggcgggag aattcggccg cacgccgaag atcacccatt gccgaagtt ctacaagctt     33360 cccgccgcg accattgggg tgccgtgcaa acggtcttct tcgccggtgg cggagtgcgt    33420 gggggacgg tgattggttc gtcggataac caaggcgggt atcccaccag cgccaaacag     33480
acgcccgaaa atatggcagc cacgatttat cagggattgg gcctgccgga tacgaccgcc    33540
tggtttgatg aaacgaaccg cccgcatcac atttattacg gtgagccgat tcctgggttg    33600
gtttagcgga gtcttgtttc tccgaaacag cttttttcaaa gctgcagatc aagagactcg    33660
acattcggag aaagttgacg gcactctgat agacgctgtt ggttcggaag aggagaattg    33720
aatgcttgag agccatcctt ttctgccggc gggtgcaccc aagcaccgga cgttttcacg    33780
gcggactgtg ttgcaggccg gtggggtgag tttgctcggt ttgggcatga atcacctcac    33840
agccttgcga actgctggag cagccgaggg tgtctcgcat tcggcttcgc cgcgagcacg    33900
ggcagtgatt tacattttcc tctcaggtgg actgggacag cacgacagct tcgacatgaa    33960
gccggaggcc cccgacaaca ttcggggtga gttccatccg attccgacca atacgccggg    34020
tatcgatgtt tgccagcact tgccgcgatt ggcccaacgc agtcacctgt ggtcgcttgt    34080
gcggtcgttg tcgcactcga cgaacggaca ttcggaaggc catttgttca tgctcaccgg    34140
gcggtcgatt ttgcctccgg ggttcaatgg cagccttccc aaaccgagcg attggccttc    34200
catggcctcg atcgccggtg cgttgatgcc tgcacggaat aatctgccgc cggctgtcgt    34260
gctgccggaa acgctgattc accgcacggg ccgcgtcatt cccggccagt ttggcggttt    34320
gatgggccgt cagcgcgatc cgtggtttat cgaagcctcg ccattcaacc ccaccagtta    34380
tggggcgttt cccaattacg aattccattt tgccggcggt gagtcgaaac atacggagag    34440
cctcaaattc caggctccga gcctctcgct tccggaaggg ctggggatgg gccggctgga    34500
tcaccgcttg ggactgctca agcacatcga acggcaacgg atcgatctcg accgggccgc    34560
gtccgcggaa aatttcgacc gctatcggca ggggctgtc tcgctgctca ccgatcaacg     34620
cgtcaaacag gctttcgacg tcgtgaatgc ggatccgaaa gtcctcgacc gatatggccg    34680
caactcgttc ggctggtcgt tgctcatggc gcgccagtac ttcggcctga aaaaccagg    34740 agaactgaac aagcatgcgt aaaggagaag aacttttcac tggagttgtc ccaattcttg    34800
ttgaattaga tggtgatgtt aatgggcaca aattttctgt cagtggagag ggtgaaggtg    34860
atgcaacata cggaaaactt acccttaaat ttatttgcac tactggaaaa ctacctgttc    34920
```

```
catggccaac acttgtcact actttcggtt atggtgttca atgctttgcg agatacccag    34980
atcatatgaa acggcatgac tttttcaaga gtgccatgcc cgaaggttat gtacaggaaa    35040
gaactatatt tttcaaagat gacgggaact acaagacacg tgctgaagtc aagtttgaag    35100
gtgatacccT tgttaataga atcgagttaa aaggtattga ttttaaagaa gatggaaaca    35160
ttcttggaca caaattggaa tacaactata actcacacaa tgtatacatc atggcagaca    35220
aacaaaagaa tggaatcaaa gttaacttca aaattagaca caacattgaa gatggaagcg    35280
ttcaactagc agaccattat caacaaaata ctccaattgg cgatggccct gtccttttac    35340
cagacaacca ttacctgtcc acacaatctg cccTttcgaa agatcccaac gaaaagagag    35400
accacatggt ccttcttgag tttgtaacag ctgctgggat tacacatggc atggatgaac    35460
tatacaaata agcttaatta gctgagcttg gactcctgtt gatagatcca gtaatgacct    35520
cagaactcca tctggatttg ttcagaacgc tcggttgccg ccgggcgttt tttattggtg    35580
agaatccaag ctagcttggc gagattttca ggagctaggc gcgccgactg gttgaagccg    35640
gcgtcagcat ggtgcaggtc aacctcggca acaacgaatc gtgggatacg cacgtttcg     35700 cgtttcccct gttgaaagac aaacttctgc caccgaccga cctggcagtt tcagcattgc    35760
tcgacgacct caacgacagc ggcctgctcg attcgacgtt gattgttatg gccggtgagt    35820
tcggtcggac tccgaagatt tcgacgttgc cgcagtttta caagctgccg ggtcgcgatc    35880
actggggcgc cgtgcagacg tcttcttttg ccggcggcgg aacgcgtggc ggtcgagtcg    35940
tcggttcatc cgacaaaatc ggcggatatc cgccaccga acgtcagact cccgaaaaca    36000
tggctgccac cgtctatcac tctttgggac ttccagacac ggcagcctgg cacgacagcg    36060
tcgatcgccc gcatcacatt taccacggcg aaccgatcac agggctgctg tagcggctgg    36120
acacgaggga atagggggcca agaattagag attgtcgaaa acaaaatgcc ggggtcatct    36180
tgtaatgaac cccggcattt ccatttatct tttctctaa ccccctacccg attacgggaa    36240 ggtgaacgaa cccggcgcca cggtcaccca gtcgaagttt cgctcgccga tggcgggaag    36300
tgcagtaatt gccgccgtcg agccgaagtt gtctgcaata cctgtgaaac ccgtagtcga    36360
ggaatcgctg gtgacctgga aggtgctgga accgacgccg tcatacttga acccaaccgc    36420
acccgtcagc aacggagtgc ccgggaggtt gaatggcggg gggttgttgt cgggcaggcg    36480
ttgggcattc cgcaaacgtg tgtccgtgag gaagggaccc gggtcggttt gagtcgtcag    36540
acgagatttg aacaagccgt cgggatctgt tggaccatag agcgccccga agcgggtcac    36600
atcgaccgag gcggcaacac cggtgttgcc gacgaattcc aaattcaggc gagccagagg    36660
atcgtgcgtg tagccgacag gcagaatgaa cgtcgtgttt gtccaagttc caccgcccgg    36720
agtcgtataa gtggccgaca cgaaggattc gatggttacg ctgaagcctg agttggactg    36780
aatgacgttg ttgtcgatac gggcattgac ctggcccaca ccattggtca gacccgaatt    36840
catggtggcg agtcctacag tagcggtcgt ctgggcattc gatgttccga cgcgaaggat    36900
caaaccggtg cccaggtcgc tgacggggct gttcgcaccg ttgaactcga tagcattgtt    36960
tctggcatcg aaaaccatgt tgggggaatt gagcgaactt ccggcactgg tcagcgtggt    37020
ggtcgtcgcg ctttgggctt ggctgttgtc ggcggtgtta accacataca cgccttcgcg    37080
acggttgctc acaatcgagt tgccgtcagt cgggctggat ccacccagta cgatgatcgt    37140
attcgcgtcg ccggcattca agatgtcgat accgcgtccc aggttcgagt cgatcacgtt    37200
gctgactgca gtcactgttg tcaggttgcc gccgttcaac cgcacgtgct cgttgcgaat    37260
cgtgataccg gtcccgttgt tcgccgagat caggttgccg tcgaacgttt cgtcgaaacc    37320
```

```
acccaggtcg ctattgttga tcaacacgcc gccgccggcc aacgaggcag acagacgacc   37380
gttgttcgaa atcgtgttat tggtgaagac gttcgtaccg tagttgcccc cggtgatgct   37440
gataccgatg aggccgttgt tgtcgatgag gttgccgttc ccggttccag ccagaccgac   37500
gatcaggctg ttggtaatcc cagccaggtt gataccgtta ccgttgttgg tctggatggt   37560
attgcccgtc cacgtgccgg agatctgcgg ctgattggct acggtgttct ggaagatcgt   37620
ggcgcggata ccgtcacccg tgttgttctg aatcttgttg gtggtcatat tgacctgcaa   37680
caggccgtcg atctcggccc gcaaggcaac gccattcccg ttgttgcctt tgatcgtgtt   37740
gttctggagg gtgtaggtgt tggtcgtcaa accaccgaac cggtcgagca ggttgatacc   37800
gtcgcccgtg ttgttctgga gtgttcctag gctgtttcct ggtgggatcc tctagagtcg   37860
acctgcaggc atgcaagctt gagtattcta tagtctcacc taaatagctt ggcgtaatca   37920
tggtcatagc tgtttcctgt gtgaaattgt tatccgctca caattccaca acatacga   37980 gccgaagca taaagtgtaa agcctggggt gcctaatgag tgagctaact cacattaatt   38040
gcgttgcgct cactgcccgc tttccagtcg ggaaacctgt cgtgccagct gcattaatga   38100
atcggccaac gcgaacccct tgcggccgcc cgggccgtcg accaattctc atgtttgaca   38160
gcttatcatc gaatttctgc cattcatccg cttattatca cttattcagg cgtagcaacc   38220
aggcgtttaa gggcaccaat aactgcctta aaaaaattac gccccgccct gccactcatc   38280
gcagtactgt tgtaattcat taagcattct gccgacatgg aagccatcac aaacggcatg   38340
atgaacctga atcgccagcg gcatcagcac cttgtcgcct tgcgtataat atttgcccat   38400
ggtgaaaacg ggggcgaaga agttgtccat attggccacg tttaaatcaa aactggtgaa   38460
actcacccag ggattggctg agacgaaaaa catattctca ataaaccctt agggaaata   38520 ggccaggttt tcaccgtaac acgccacatc ttgcgaatat atgtgtagaa actgccggaa   38580
atcgtcgtgg tattcactcc agagcgatga aaacgtttca gtttgctcat ggaaaacggt   38640
gtaacaaggg tgaacactat cccatatcac cagctcaccg tctttcattg ccatacgaaa   38700
ttccggatga gcattcatca ggcgggcaag aatgtgaata aaggccggat aaaacttgtg   38760 cttattttc tttacggtct ttaaaaaggc cgtaatatcc agctgaacgg tctggttata   38820
ggtacattga gcaactgact gaaatgcctc aaaatgttct ttacgatgcc attgggatat   38880
atcaacggtg gtatatccag tgatttttt ctccatttta gcttccttag ctcctgaaaa   38940
tctcgataac tcaaaaaata cgcccggtag tgatcttatt tcattatggt gaaagttgga   39000
acctcttacg tgccgatcaa cgtctcattt tcgccaaaag ttggcccagg cttcccggt   39060 atcaacaggg acaccaggat ttatttattc tgcgaagtga tcttccgtca caggtattta   39120
ttcgcgataa gctcatggag cggcgtaacc gtcgcacagg aaggacagag aaagcgcgga   39180
tctgggaagt gacggacaga acggtcagga cctggattgg ggaggcggtt gccgccgctg   39240
ctgctgacgt tgtgacgttc tctgttccgg tcacaccaca tacgttccgc cattcctatg   39300
cgatgcacat gctgtatgcc ggtataccgc tgaaagttct gcaaagcctg atgggacata   39360
agtccatcag ttcaacggaa gtctacacga aggttttgc gctggatgtg gctgcccggc   39420
accgggtgca gtttgcgatg ccggagtctg atgcggttgc gatgctgaaa caattatcct   39480
gagaataaat gccttggcct ttatatggaa atgtggaact gagtggatat gctgtttttg   39540
tctgttaaac agagaagctg gctgttatcc actgagaagc gaacgaaaca gtcgggaaaa   39600
tctcccatta tcgtagagat ccgcattatt aatctcagga gcctgtgtag cgtttatagg   39660
```

| | |
|---|---|
| aagtagtgtt ctgtcatgat gcctgcaagc ggtaacgaaa acgatttgaa tatgccttca | 39720 |
| ggaacaatag aaatcttcgt gcggtgttac gttgaagtgg agcggattat gtcagcaatg | 39780 |
| gacagaacaa cctaatgaac acagaaccat gatgtggtct gtcctttac agccagtagt | 39840 |
| gctcgccgca gtcgagcgac agggcgaagc cctcggctgg ttgccctcgc cgctgggctg | 39900 |
| gcggccgtct atggccctgc aaacgcgcca gaaacgccgt cgaagccgtg tgcgagacac | 39960 |
| cgcggccggc cgccggcgtt gtggatacct cgcggaaaac ttggccctca ctgacagatg | 40020 |
| aggggcggac gttgacactt gaggggccga ctcacccggc gcggcgttga cagatgaggg | 40080 |
| gcaggctcga tttcggccgg cgacgtggag ctggccagcc tcgcaaatcg gcgaaaacgc | 40140 |
| ctgattttac gcgagtttcc cacagatgat gtggacaagc ctggggataa gtgccctgcg | 40200 |
| gtattgacac ttgaggggcg cgactactga cagatgaggg gcgcgatcct tgacacttga | 40260 |
| ggggcagagt gctgacagat gaggggcgca cctattgaca tttgaggggc tgtccacagg | 40320 |
| cagaaaatcc agcatttgca agggtttccg cccgttttc ggccaccgct aacctgtctt | 40380 |
| ttaacctgct tttaaaccaa tatttataaa ccttgttttt aaccagggct gcgccctgtg | 40440 |
| cgcgtgaccg cgcacgccga aggggggtgc cccccttct cgaaccctcc cggtcgagtg | 40500 |
| agcgaggaag caccagggaa cagcacttat atattctgct tacacacgat gcctgaaaaa | 40560 |
| acttcccttg gggttatcca cttatccacg gggatatttt tataattatt ttttttatag | 40620 |
| ttttagatc ttctttttta gagcgccttg taggccttta tccatgctgg ttctagaaa | 40680 |
| ggtgttgtga caaattgccc tttcagtgtg acaaatcacc ctcaaatgac agtcctgtct | 40740 |
| gtgacaaatt gcccttaacc ctgtgacaaa ttgccctcag aagaagctgt tttttcacaa | 40800 |
| agttatccct gcttattgac tctttttat ttagtgtgac aatctaaaaa cttgtcacac | 40860 |
| ttcacatgga tctgtcatgg cggaaacagc ggttatcaat cacaagaaac gtaaaaatag | 40920 |
| cccgcgaatc gtccagtcaa acgacctcac tgaggcggca tatagtctct cccgggatca | 40980 |
| aaaacgtatg ctgtatctgt tcgttgacca gatcagaaaa tctgatggca ccctacagga | 41040 |
| acatgacggt atctgcgaga tccatgttgc taaatatgct gaaatattcg gattgacctc | 41100 |
| tgcggaagcc agtaaggata tacgcaggc attgaagagt ttcgcgggga aggaagtggt | 41160 |
| tttttatcgc cctgaagagg atgccggcga tgaaaaggc tatgaatctt ttccttggtt | 41220 |
| tatcaaacgt gcgcacagtc catccagagg gctttacagt gtacatatca acccatatct | 41280 |
| cattcccttc tttatcgggt tacagaaccg gtttacgcag tttcggctta gtgaaacaaa | 41340 |
| agaaatcacc aatccgtatg ccatgcgttt atacgaatcc ctgtgtcagt atcgtaagcc | 41400 |
| ggatggctca ggcatcgtct ctctgaaaat cgactggatc atagagcgtt accagctgcc | 41460 |
| tcaaagttac cagcgtatgc ctgacttccg ccgccgcttc ctgcaggtct gtgttaatga | 41520 |
| gatcaacagc agaactccaa tgcgcctctc atacattgag aaaagaaag gccgccagac | 41580 |
| gactcatatc gtattttcct tccgcgatat cacttccatg acgacaggat agtctgaggg | 41640 |
| ttatctgtca cagatttgag ggtggttcgt cacatttgtt ctgacctact gagggtaatt | 41700 |
| tgtcacagtt ttgctgtttc cttcagcctg catggatttt ctcatacttt ttgaactgta | 41760 |
| atttttaagg aagccaaatt tgagggcagt ttgtcacagt tgatttcctt ctctttccct | 41820 |
| tcgtcatgtg acctgatatc ggggttagt tcgtcatcat tgatgagggt tgattatcac | 41880 |
| agtttattac tctgaattgg ctatccgcgt gtgtacctct acctggagtt tttcccacgg | 41940 |
| tggatatttc ttcttgcgct gagcgtaaga gctatcgac agaacagttc ttctttgctt | 42000 |
| cctcgccagt tcgctcgcta tgctcggtta cacggctgcg gcgagcgcta gtgataataa | 42060 |

```
gtgactgagg tatgtgctct tcttatctcc ttttgtagtg ttgctcttat tttaaacaac   42120
tttgcggttt tttgatgact ttgcgatttt gttgttgctt tgcagtaaat tgcaagattt   42180
aataaaaaaa cgcaaagcaa tgattaaagg atgttcagaa tgaaactcat ggaaacactt   42240
aaccagtgca taaacgctgg tcatgaaatg acgaaggcta tcgccattgc acagtttaat   42300
gatgacagcc cggaagcgag gaaaataacc cggcgctgga gaataggtga agcagcggat   42360
ttagttgggg tttcttctca ggctatcaga gatgccgaga aagcagggcg actaccgcac   42420
ccggatatgg aaattcgagg acgggttgag caacgtgttg gttatacaat tgaacaaatt   42480
aatcatatgc gtgatgtgtt tggtacgcga ttgcgacgtg ctgaagacgt atttccaccg   42540
gtgatcgggg ttgctgccca taaaggtggc gtttacaaaa cctcagtttc tgttcatctt   42600
gctcaggatc tggctctgaa ggggctacgt gttttgctcg tggaaggtaa cgaccccag   42660 ggaacagcct caatgtatca cggatgggta ccagatcttc atattcatgc agaagacact   42720
ctcctgcctt tctatcttgg ggaaaaggac gatgtcactt atgcaataaa gcccacttgc   42780
tggccggggc ttgacattat tccttcctgt ctggctctgc accgtattga aactgagtta   42840
atgggcaaat ttgatgaagg taaactgccc accgatccac acctgatgct ccgactggcc   42900
attgaaactg ttgctcatga ctatgatgtc atagttattg acagcgcgcc taacctgggt   42960
atcggcacga ttaatgtcgt atgtgctgct gatgtgctga ttgttccac gcctgctgag   43020 ttgtttgact acacctccgc actgcagttt ttcgatatgc ttcgtgatct gctcaagaac   43080
gttgatctta aagggttcga gcctgatgta cgtattttgc ttaccaaata cagcaatagt   43140
aatggctctc agtccccgtg gatggaggag caaattcggg atgcctgggg aagcatggtt   43200
ctaaaaaatg ttgtacgtga aacggatgaa gttggtaaag gtcagatccg gatgagaact   43260 gttttttgaac aggccattga tcaacgctct tcaactggtg cctggagaaa tgctctttct   43320
atttgggaac ctgtctgcaa tgaaattttc gatcgtctga ttaaaccacg ctgggagatt   43380
agataatgaa gcgtgcgcct gttattccaa aacatacgct caatactcaa ccggttgaag   43440
atacttcgtt atcgacacca gctgccccga tggtggattc gttaattgcg cgcgtaggag   43500
taatggctcg cggtaatgcc attactttgc ctgtatgtgg tcgggatgtg aagtttactc   43560
ttgaagtgct ccgggtgat agtgttgaga agacctctcg ggtatggtca ggtaatgaac   43620
gtgaccagga gctgcttact gaggacgcac tggatgatct catcccttct tttctactga   43680
ctggtcaaca gacaccggcg ttcggtcgaa gagtatctgg tgtcatagaa attgccgatg   43740
ggagtcgccg tcgtaaagct gctgcactta ccgaaagtga ttatcgtgtt ctggttggcg   43800
agctggatga tgagcagatg gctgcattat ccagattggg taacgattat cgcccaacaa   43860
gtgcttatga acgtggtcag cgttatgcaa gccgattgca gaatgaattt gctgaaaata   43920
tttctgcgct ggctgatgcg gaaaatattt cacgtaagat tattacccgc tgtatcaaca   43980
ccgccaaatt gcctaaatca gttgttgctc ttttttctca ccccggtgaa ctatctgccc   44040
ggtcaggtga tgcacttcaa aaagccttta cagataaaga ggaattactt aagcagcagg   44100
catctaacct tcatgagcag aaaaaagctg gggtgatatt tgaagctgaa gaagttatca   44160
ctcttttaac ttctgtgctt aaaacgtcat ctgcatcaag aactagttta agctcacgac   44220
atcagtttgc tcctggagcg acagtattgt ataagggcga taaaatggtg cttaacctgg   44280
acaggtctcg tgttccaact gagtgtatag agaaaattga ggccattctt aaggaacttg   44340
aaaagccagc accctgatgc gaccacgttt tagtctacgt ttatctgtct ttacttaatg   44400
```

```
tcctttgtta caggccagaa agcataactg gcctgaatat tctctctggg cccactgttc    44460
cacttgtatc gtcggtctga taatcagact gggaccacgg tcccactcgt atcgtcggtc    44520
tgattattag tctgggacca cggtcccact cgtatcgtcg gtctgattat tagtctggga    44580
ccacggtccc actcgtatcg tcggtctgat aatcagactg ggaccacggt cccactcgta    44640
tcgtcggtct gattattagt ctgggaccat ggtcccactc gtatcgtcgg tctgattatt    44700
agtctgggac cacggtccca ctcgtatcgt cggtctgatt attagtctgg aaccacggtc    44760
ccactcgtat cgtcggtctg attattagtc tgggaccacg gtcccactcg tatcgtcggt    44820
ctgattatta gtctgggacc acgatcccac tcgtgttgtc ggtctgatta tcggtctggg    44880
accacggtcc cacttgtatt gtcgatcaga ctatcagcgt gagactacga ttccatcaat    44940
gcctgtcaag ggcaagtatt gacatgtcgt cgtaacctgt agaacggagt aacctcggtg    45000
tgcggttgta tgcctgctgt ggattgctgc tgtgtcctgc ttatccacaa cattttgcgc    45060
acggttatgt ggacaaaata cctggttacc caggccgtgc cggcacgtta accgggctgc    45120
atccgatgca agtgtgtcgc tgtcgacgag ctcgcgagct cggacatgag gttgcccgt    45180 attcagtgtc gctgatttgt attgtctgaa gttgttttta cgttaagttg atgcagatca    45240
attaatacga tacctgcgtc ataattgatt atttgacgtg gtttgatggc ctccacgcac    45300
gttgtgatat gtagatgata atcattatca ctttacgggt cctttccggt gatccgacag    45360
gttacggggc ggcgacctcg cgggttttcg ctatttatga aaattttccg gtttaaggcg    45420
tttccgttct tcttcgtcat aacttaatgt ttttatttaa aataccctct gaaaagaaag    45480
gaaacgacag gtgctgaaag cgagcttttt ggcctctgtc gtttcctttc tctgtttttg    45540
tccgtggaat gaacaatgga agtccgagct catcgctaat aacttcgtat agcatacatt    45600
atacgaagtt atattcgat                                                  45619
```